US012800592B2

(12) United States Patent
Haskins et al.

(10) Patent No.: US 12,800,592 B2
(45) Date of Patent: Nov. 17, 2026

(54) COMBINATORIAL TEMPORAL BIOMARKERS AND PRECISION MEDICINES WITH DETECTION AND TREATMENT METHODS FOR USE IN NEURO INJURY, NEURO DISEASE, AND NEURO REPAIR

(71) Applicants: GRYPHON BIO, INC., South San Francisco, CA (US); University of Florida Research Foundation, Inc., Gainesville, FL (US)

(72) Inventors: William E. Haskins, South San Francisco, CA (US); Kevin Ka-wang Wang, Gainesville, FL (US)

(73) Assignees: Gryphon Bio, Inc., South San Francisco, CA (US); University of Florida Research Foundation, Inc., Gainesville, FL (US)

( * ) Notice: Subject to any disclaimer, the term of this patent is extended or adjusted under 35 U.S.C. 154(b) by 1133 days.

(21) Appl. No.: 17/413,747

(22) PCT Filed: Dec. 13, 2019

(86) PCT No.: PCT/US2019/066346
§ 371 (c)(1),
(2) Date: Jun. 14, 2021

(87) PCT Pub. No.: WO2020/124013
PCT Pub. Date: Jun. 18, 2020

(65) Prior Publication Data

US 2022/0057409 A1 Feb. 24, 2022

Related U.S. Application Data

(60) Provisional application No. 62/779,051, filed on Dec. 13, 2018.

(51) Int. Cl.
*G01N 33/68* (2006.01)

(52) U.S. Cl.
CPC ..... *G01N 33/6893* (2013.01); *G01N 2800/56* (2013.01); *G01N 2800/60* (2013.01)

(58) Field of Classification Search
CPC ........... G01N 33/6893; G01N 2800/56; G01N 2800/60
See application file for complete search history.

(56) References Cited

U.S. PATENT DOCUMENTS 9,482,675 B1 * 11/2016 Lovell .............. G01N 33/54388
2003/0119064 A1 * 6/2003 Valkirs ................ G01N 33/573 435/7.1

(Continued)

FOREIGN PATENT DOCUMENTS

EP 2321355 B1 8/2017
WO 2015157390 A1 10/2015

(Continued)

OTHER PUBLICATIONS

Farmer, et al., "Resolving Astrocyte Heterogeneity in the CNS", Frontiers in Cellular Neuroscience, Sep. 2017, vol. 11, Art. 300, pp. 2-7.

(Continued)

*Primary Examiner* — Lyle Alexander
*Assistant Examiner* — Dwan A Gerido
(74) *Attorney, Agent, or Firm* — MaxGoLaw PLLC

(57) ABSTRACT

A method, device, and kit are provided for temporal diagnostics and clinical treatment of neuro injury, neuro disease, or neuro repair, particularly including clinical treatment with precision medicines for the same therapeutic targets as a subset of the temporal biomarkers. Through the measurement of biomarkers in a biological sample from a subject, with at least one biomarker from each of the early, inter- (Continued)

mediate, and late phases of suspected injury, disease, or repair from a subject, a determination of a subject's injury, disease, or repair is provided with greater sensitivity and/or specificity than previously attainable. As many clinical inventions such an anti-inflammatories and clot disruptors are effective only during certain phases injury, disease, or repair, this knowledge can be used to clinical effect in mitigating secondary injuries and/or diseases.

5 Claims, 20 Drawing Sheets

(56) References Cited

U.S. PATENT DOCUMENTS

2003/0199000 A1* 10/2003 Valkirs ................. G01N 33/573 435/7.1
2008/0131881 A1* 6/2008 Ladenson ............ C12Q 1/6883 435/327
2014/0018299 A1* 1/2014 Mondello .......... G01N 33/6896 514/17.7
2014/0377763 A1* 12/2014 Montaner Villalonga .................. C12Q 1/6883 435/6.12
2015/0141528 A1 5/2015 Larner
2016/0154101 A1 6/2016 Kim et al.
2017/0176460 A1 6/2017 Lamer
2017/0315136 A9 11/2017 Wang et al.
2019/0242906 A1* 8/2019 McQuiston ........ G01N 33/6893
2019/0376983 A1* 12/2019 McQuiston .......... A61B 5/0042
2021/0096140 A1* 4/2021 Hrusovsky ........... A61B 5/0071

FOREIGN PATENT DOCUMENTS

WO WO2015157390 * 10/2015
WO 2016081100 A1 5/2016

OTHER PUBLICATIONS

Office Action issued in corresponding European Appln. No. 19897288.7, dated Jun. 18, 2024.
Int'l Search Report for PCT/US2019/066346, dated Apr. 17, 2020.
Gyorgy, A. et al., "Time-dependent changes in serum biomarker levels after blast traumatic brain injury," Journal of neurotrauma, Jun. 2011, vol. 28, pp. 1121-1126 (abstract).
Supplementary European Search Report issued in EP19897373.7, dated Sep. 6, 2022.
Wilhelmsson, et al., "Absence of Glial Fibrillary Acidic Protein and Vimentin Prevents Hypertrophy of Astrocytic Processes and Improves Post-Traumatic Regeneration", The Journal of Neuroscience, vol. 24, No. 21, May 26, 2004 (May 26, 2004), pp. 5016-5021.
Eng, et al., "GFAP and Astrogliosis", Brain Pathology, vol. 4, No. 3, Jul. 1, 1994 (Jul. 1, 1994), pp. 229-237.
O'Callaghan, et al., "Quantitative aspects of drug and toxicant-induced astrogliosis", Neurochemistry International, Elsevier, Amsterdam, NL, vol. 26, No. 2, Feb. 1, 1995 (Feb. 1, 1995), pp. 115-124.
Peng, et al., "Neuroprotective effect of active immunity with purified recombinant protein GFAP on spinal cord injury", Journal of Traumatic Surgery, vol. 13, No. 3, May 15, 2011 (May 15, 2011), pp. 244-249.
Hagemann, et al., "Antisense suppression of glial fibrillary acidic protein as a treatment for Alexander disease", Annals of Neurology, vol. 83, No. 1, Jan. 2018 (Jan. 2018 ),—Jan. 14, 2019 (Jan. 14, 2019), pp. 27-39.
Supplementary European Search Report issued in EP19897288, dated Aug. 10, 2022.
Adrian, et al., "Biomarkers of Traumatic Brain Injury: Temporal Changes in Body Fluids", ENEURO, vol. 3, No. 6, Nov. 1, 2016.
Wang, et al., "An updated on diagnostic and prognostic biomarkers for traumatic brain injury", Expert Reviews in Molecular Diagnostics, vol. 18, No. 2, Jan. 23, 2018, pp. 165-180.
Browning, et al., "Levetiracetam Treatment in Traumatic Brain Injury: Operation Brain Trauma Therapy", Journal of Neurotrauma, vol. 33, No. 6, Mar. 15, 2016, pp. 581-594.

* cited by examiner

Tissue and Tau and p-Tau levels in LEV-treated animals

Tissue and Tau and p-Tau levels in LEV-treated animals

Tissue and Tau and p-Tau levels in LEV-treated animals

T-Tau p-Tau p-Tau/T-Tau

Set 1 mice: 10 days post-CCI

Set 2 mice: 20 days post-CCI

Set 3 mice: 50 days post-CCI

COMBINATORIAL TEMPORAL BIOMARKERS AND PRECISION MEDICINES WITH DETECTION AND TREATMENT METHODS FOR USE IN NEURO INJURY, NEURO DISEASE, AND NEURO REPAIR

RELATED APPLICATIONS

This application claims priority benefit of U.S. Provisional Application Ser. No. 62/779,051 filed 13 Dec. 2018, the contents of which are hereby incorporated by reference.

FIELD OF THE INVENTION

The present invention in general relates to neuro injury, neuro disease, and neuro repair and in particular to a combination-based panel of temporal biomarkers that are composed of at least one biomarker from the early phase subset, at least one biomarker from the intermediate subset, and one biomarker from the late phase subset to afford superior temporal diagnostics and clinical treatment, particularly including clinical treatment with precision medicines for the same therapeutic targets as a subset of the temporal biomarkers. The present invention also relates to temporal biomarkers as companion diagnostics for these precision medicines, with scoring algorithms and correlations to molecular or clinical knowledgebases. The present invention also relates to combination detection of a subset of temporal biomarkers to enhance detection, particularly the late phase subset including total Tau protein and phosphorylated Tau protein based on one of the following methods: (1) combination measurement of at least three phosphorylated epitopes of Tau, (2) combination measurement using a sandwich immunoassay with a total Tau antibody or aptamer and the combined use of phospho-Serine, phospho-Threonine and/or phospho-Tyrosine-specific antibodies or aptamers, and (3) combination measurement using a sandwich immunoassay with a total Tau antibody or aptamer and the combined use of proline-phospho-serine-, and proline-phospho-threonine-specific antibodies or aptamers.

BACKGROUND OF THE INVENTION

The scientific and medical fields of neuro injury, neuro disease, and neuro repair (referred to herein as injury, disease and repair hereafter) remain frustrated by the recognition that secondary injury or disease to central nervous system (CNS) or peripheral nervous system (PNS) tissue associated with physiologic response to the initial insult, disease, or repair activity could be beneficially modulated, before stress on neuronal tissues reached a preselected threshold, with rapid diagnosis and treatment. For example, traumatic, ischemic, and neurotoxic chemical insult, along with genetic disorders, all present the prospect of injury. Traumatic, ischemic, and neurotoxic chemical insult also present the prospect of other neurological and neurodegenerative diseases.

One of many injury or disease conditions, traumatic brain injury (TBI) occurs when external forces, through direct impact or acceleration, traumatically injure the brain often through falls, vehicle accidents, and violence. TBI can be characterized by its severity, from mild to severe, and the effects of such injury can be physical, cognitive, social, emotional, or behavioral and clinical outcomes range from complete recovery to permanent disability and death. TBI is a leading cause of mortality and morbidity around the world with a broad spectrum of symptoms and disabilities. There are approximately 1.7-2.0 million incidents of TBI annually. Among all ages, unintentional injuries are the fourth leading cause of death, with over 136,000 lives lost annually. Millions of others suffer a non-fatal injury each year. Injury can also manifest in the form of neurodegenerative and neurological disease(s). For example, TBI is also a risk factor for Parkinson disease (PD), Alzheimer's disease, chronic traumatic encephalopathy (CTE), epilepsy, Huntington's disease (HD), amyotrophic lateral sclerosis (ALS), frontal temporal dementia and other forms of dementia. However, to date, there are still no FDA-approved therapies to treat any forms of TBI, including treatment for repair. Similarly, there are few treatment options, including treatment for repair, for most, including the following conditions: stroke (ischemic and hemorrhagic), glioblastoma, vanishing white matter disease, and brain hemorrhage (intracerebral hemorrhage, subarachnoid hemorrhage).

Moreover, because of the similar symptoms of several other neurodegenerative and neurological diseases such as, stroke, subarachnoid hemorrhage, and multiple sclerosis (MS) and often unknown phase of the disease in individual patients (e.g., relapse vs. remission for MS patients), distinguishing one injury or disease or repair type from another has frustrated clinicians for years. Thus, there is an unmet medical need to characterize the underlying molecular pathology and temporal profile in order to classify and distinguish injury, disease, and repair for individual patients.

More common methods and areas of continuing research for clinical diagnosis of injury, disease, and repair usually involve an examination and assigning a score to an individual (e.g., Glasgow Coma Score or GCS for TBI and expanded disability status scale or EDSS for MS). These methods are of limited value and often preclude a nuanced diagnosis due to the subjectivity of the testing, and the ability of a patient to knowingly alter their true response to achieve a desired result. Neuroimaging, such as computed tomography (CT) and magnetic resonance imaging (MRI) are also widely used to help determine the scope of injury or disease and potential for intervention for repair. However, these tests are both costly and time consuming, as well as frustrated by the same problems of having an inability to distinguish one injury, disease, and repair type from another. In addition, individuals with only mild or moderate injury or disease may be unaware damage has occurred and fail to seek treatment for repair. Likewise, individuals (and their physicians) might be unaware that their injury or disease is beginning to become refractory or responsive to a current repair treatment and thus should or shouldn't seek new treatment options, respectively. It should be appreciated that repeated mild to moderate injuries (e.g., repetitive TBI) or diseases (e.g., multiple relapses in MS) can have a cumulative effect and result in a prognosis of poor repair and poor clinical outcome.

Early clinical diagnosis of injury, disease, and repair continues to be an area requiring further development. Early diagnosis can minimize injury and disease and maximize repair by facilitating earlier intervention. Much emphasis is being placed on developing biomarkers as early indicators of CNS injury, disease and repair. For example, upon injury to or disease activity in the brain, otherwise isolated brain-derived proteins are released in to the interstitial fluid of the brain and eventually cross the blood brain barrier where they can be more easily measured as peripheral biomarkers of injury, disease, and repair. Identifying specific proteins and measuring the concentrations (levels) that enter circulation before or after the onset of clinically observable injury, disease, or repair can provide an effective early means of detecting the phase, severity and type of the injury, disease or repair, as well as provide various clinical and medical utilities as described below.

A number of otherwise isolated brain-derived protein biomarkers found in the bloodstream have been identified as being associated with clinical diagnosis of injury, disease, or repair. These biomarkers are found in biofluids after injury, before and after disease, and before and after repair. However, the kinetics (concentration and time trajectories) of release of these biomarkers into circulation remains complicated for assessing the phase, type and amplitude (severity) of the injury, disease, or repair and for determining appropriate clinical responses and treatments for individual patients since each patient, injury, disease or repair is in fact unique. Injured brain cells or degenerating brain cells can release additional substance that are known to include: exosomes (with CD61 cell surface marker); and microvesicles (MV) (e.g., with MV surface glutamate receptor if MV originated from glutamatergic neurons, with Glu transporter if MV originated from astroglia, or CD11b, CD45, CD68, Triggering Receptor Expressed On Myeloid Cells 2, (TREM2), Signal Regulatory Protein Alpha (SIRPα), if MV originated from microglia/macrophage. Exosomes/MVs are released from affected brain cells into extracellular fluid and other body biofluid [e.g., lymphatic fluid, cerebrospinal fluid (CSF), blood] that offer the prospect of detection and therefore clinical intervention based on the detection. Yet, exosomes and MVs have not previously been considered to serve as circulatory biomarkers.

As a result, the reliability of biomarkers as a measure of injury, disease or repair depends upon the ability to assess the phase, type and amplitude (severity) of injury, disease, or repair. Thus, there exists the need to track the progression of injury, disease, or repair as a function of time, including the frequency and amplitude (severity) of temporal biomarker concentration waves. There also remains an unmet need for clinical intervention through the use of an in vitro diagnostic device to identify temporal biomarkers so that subject results may be obtained rapidly in any medical setting to direct the proper course of treatment for repair of subjects with an injury or disease; something currently not provided by either CT or MRI scans. There also exists a need to use exosomes, MV, or a combination thereof, to enrich for temporal biomarkers found in biofluids.

SUMMARY OF THE INVENTION

A method is provided for using an in vitro diagnostic device for detecting the phase, type or amplitude (severity) of an injury, disease, or repair in a subject. The method includes obtaining a biological sample from a subject, and applying the sample to the in vitro diagnostic device. An assay includes an early agent for detecting one or more early biomarkers of the injury, disease or repair associated with an early phase of the injury, disease or repair; an intermediate agent for detecting one or more intermediate biomarkers of the injury, disease or repair associated with an intermediate phase of the injury, disease or repair; and a late agent for detecting one or more late biomarkers of the injury, disease or repair associated with a late phase of the injury, disease or repair. The method further includes analyzing the sample to detect the amounts of the one or more early, intermediate, and late biomarkers present in the sample associated with the phase of the injury, disease, or repair.

A kit is provided for implementing the disclosed method. The kit includes a substrate for holding a sample isolated from a subject, as well as agents for detecting biomarkers. The agents include an early agent for detecting one or more early biomarkers of the injury, disease, or repair associated with an early phase of the injury, disease, or repair; an intermediate agent for detecting one or more intermediate biomarkers of the injury, disease or repair associated with an intermediate phase of the injury, disease or repair; and a late agent for detecting one or more late biomarkers of the injury, disease or repair associated with a late phase of the injury, disease or repair. Printed instructions are also included in the kit for reacting the early agent, the intermediate agent, and the late agent with the sample or a portion of the sample.

An in vitro diagnostic device is provided for detecting a neuro injury, neuro disease or neuro repair in a subject. The device includes a sample chamber for holding a biological sample collected from the subject, an assay module in fluid communication with the sample chamber, and a user interface. The assay module includes the early agent, the intermediate agent, and the late agent, and analyzes the first biological sample to detect the amounts of the one or more early, intermediate, and late biomarkers present in the sample. The user interface relates the amount of the one or more biomarkers measured in the assay module to detecting an injury, disease, or repair in the subject or the severity of injury, disease, or repair in the subject.

A method is provided for treatment of neuro injury, neuro disease, or neuro repair with precision medicines targeting the one or more early, intermediate, and late biomarkers.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings wherein:

FIGS. 13A-1-13C-2 are a series of graphs showing the efficacy of temporal pharmacodynamic (PD) biomarker-powered precision medicines for targeting SV2A;

FIGS. 16A-1-16C-2 illustrate chronic tauopathy after TBI, with a higher total-tau or P-tau expression in either cortex (IC) or hippocampus tissues (HC) at Day 50 compared to that at Day 20; FIG. 17A shows the frequency in open arms, and FIG. 17B shows the time spent in open arms.

DETAILED DESCRIPTION OF THE PREFERRED EMBODIMENTS

Figure 1:
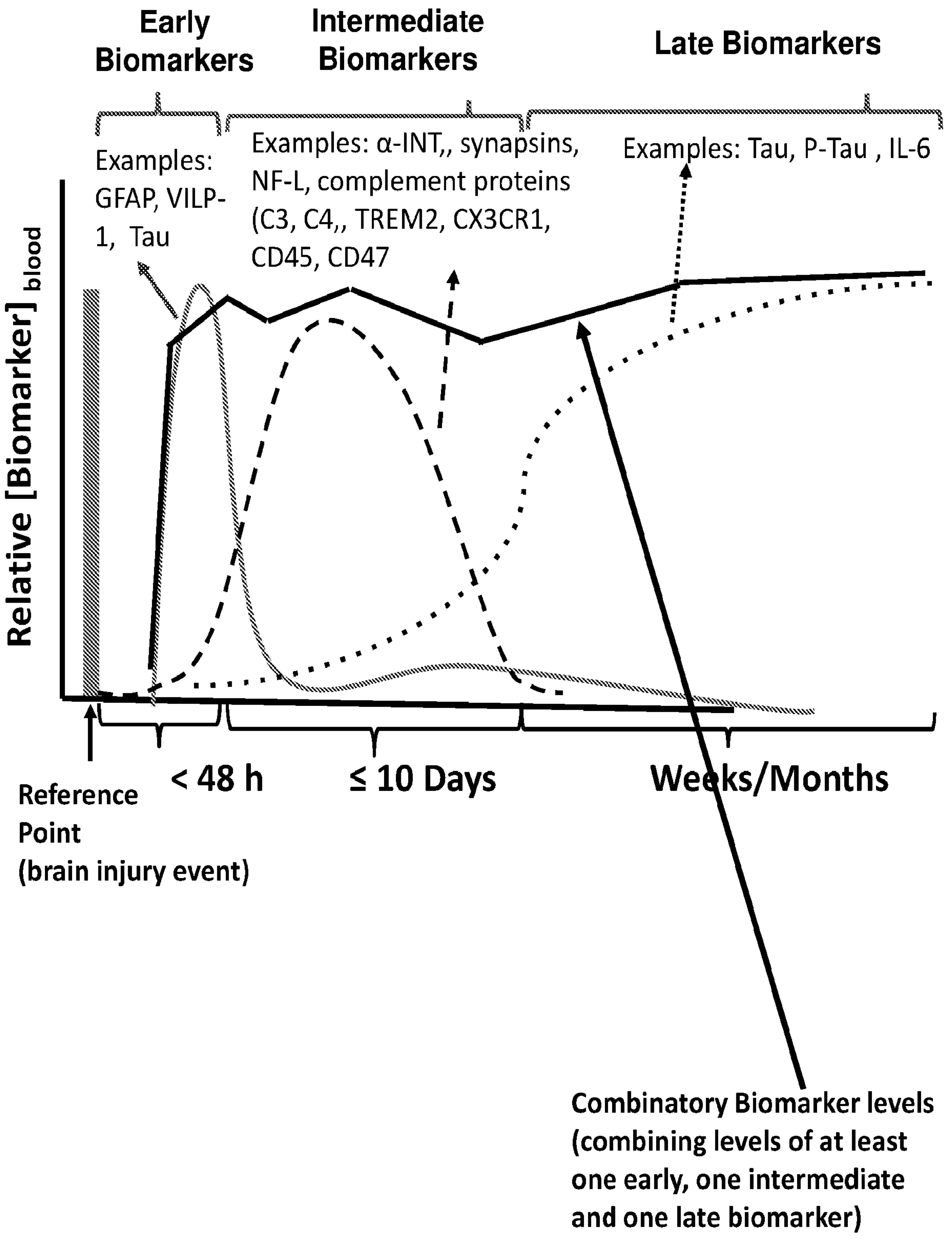
FIG. 1 is a schematic of neuro injury, neuro disease, or neuro repair measured with temporal trajectories of precision biomarkers in biofluids and the composite levels of these biomarkers over time that, in a combinatorial approach, measures concentration (levels) of at least one each of early, intermediate, and late biomarkers from a given reference point (e.g., post-injury, disease or repair event, albeit pre-injury, disease and repair measurements from the reference point of the event, or pre-events, are also described herein) to achieve sustained and detectable overall precision biomarker signals in biofluids over these different phases of injury, disease or repair.

The present invention has utility in the superior temporal diagnostics and clinical treatment of neuro injury, neuro disease, or neuro repair (referred to as injury, disease and repair hereafter) particularly including clinical treatment with precision medicines for the same therapeutic targets as a subset of the temporal biomarkers. Through the measurement of biomarkers in a biological sample from a subject, with at least one biomarker from each of the early, intermediate, and late phases of suspected injury, disease, or repair from a subject, a determination of a subject's injury, disease, or repair is provided with greater sensitivity and/or specificity than previously attainable. As many clinical inventions such an anti-inflammatories and clot disruptors are effective only during certain phases injury, disease, or repair, this knowledge can be used to clinical effect in mitigating secondary injuries and/or diseases. Surprisingly, by combining the detection of these temporal biomarkers, a synergistic result is achieved. More surprisingly, by combining the detection of these temporal biomarkers with specific treatments at each phase of injury, disease, or repair, a synergistic result is achieved.

The present invention also has utility in the use of temporal biomarkers as companion diagnostics for these precision medicines, with scoring algorithms and correlations to molecular or clinical knowledgebases. The combination detection of a subset of temporal biomarkers to enhance detection, particularly the late phase subset including total Tau protein and phosphorylated Tau protein based on one of the following methods: (1) combination measurement of at least three phosphorylated epitopes of Tau, (2) combination measurement using a sandwich immunoassay with a total Tau antibody or aptamer and the combined use of phospho-Serine, phospho-Threonine and/or phospho-Tyrosine-specific antibodies or aptamers, and (3) combination measurement using a sandwich immunoassay with a total Tau antibody or aptamer and the combined use of proline-phospho-serine-, and proline-phospho-threonine-specific antibodies or aptamers affords clinical detection and treatment options not currently available.

An inventive combinatorial biomarker assay provides a panel for injury, disease, or repair can provide uniquely useful characteristics and information that are absent when one singular or individual biomarker is used. As a result, the present invention is particularly powerful to provide an individual patient who suffers from a form of injury (e.g., TBI), disease, or repair is likely to have its unique pathological signature, as well its own temporal magnification and trajectory (type, phase and amplitude) of disease and repair (progression and recovery). In terms of clinical and medical utilities, the present invention has utility as a companion diagnostic for precision medicines, with scoring algorithms and correlations to molecular or clinical knowledgebases, and utilities as diagnostic, monitoring, pharmacodynamic/response, predictive, prognostic, safety, or susceptibility/risk biomarkers. The combinatorial precision biomarkers can be assessed and quantified by using combinatorial detection methods (including antibody and aptamer-based detection agents) for temporal diagnostics of injury, disease, or repair, and can also be used to accelerate drug development for preclinical and clinical studies, including: enrichment of treatment-responding subjects/patients, guiding of treatment (e.g., drug combinations, dose and frequency) and surrogate endpoints for safety, efficacy and cognitive improvement. By way of example, levels of combinatorial precision biomarkers in biofluids can be correlated to injury, disease, and repair clinical measures such as Glasgow coma scale (GCS) or cranial computed tomography (CT) abnormality, magnetic resonance imaging (MRI) detectability abnormality, neurological outcome scoring systems such as Glasgow outcome score, (GOS) and GOS-extended (GOSE) and Disability rating scale (DRS) (commonly used in TBI), Modified Rankin scale (commonly used in stroke) and cerebral performance category (CPC).

A detection method, kits and in vitro diagnostic devices specifically designed and calibrated to detect biomarkers that are differentially present in the samples of patients suffering from injury, disease, or repair including neurotoxicity or neuroprotection and nerve cell damage or growth are provided. These devices aid in diagnosis of injury, disease, or repair by detecting and determining the concentrations (levels) and/or trajectories of temporal biomarkers that are indicative to the respective injury, disease, or repair type through temporal combinatorial analysis. The measurement of these temporal biomarkers in combination in patient samples provides information that a diagnostician can correlate with a probable diagnosis and prognosis for an injury or disease such as sports concussion, TBI, and stroke, as well as the repair of the condition.

In certain embodiments, an in vitro diagnostic device is provided to measure biomarkers that are indicative of various levels of TBI (that can be associated with gunshot wounds, automobile accidents, explosions, sports accidents, shaken baby syndrome), stroke (ischemic and hemorrhagic), spinal cord injury (SCI), and brain hemorrhage (intracerebral hemorrhage, subarachnoid hemorrhage), Parkinson disease (PD), chronic traumatic encephalopathy (CTE), Alzheimer's disease (AD), chronic traumatic encephalopathy (CTE), epilepsy, Huntington's disease (HD), amyotrophic lateral sclerosis (ALS), frontal temporal dementia and other forms of dementia, hypoxic ischemic encephalopathy (HIE), mild to moderate to complicated mild to severe TBI, vanishing white matter disease, neural damage due to drug or alcohol addiction (e.g., from amphetamines, Ecstasy/MDMA, or ethanol), or other diseases and disorders associated with the CNS or PNS, such as prion-related disease; diabetic neuropathy, multiple sclerosis (MS), chemotherapy-induced neuropathy, peripheral neuropathy and neuropathic pain.

In other embodiments, the biomarkers are proteins, fragments or derivatives thereof, and are absent an aforementioned condition are associated with neuronal cells, brain cells or any cell that is present in the brain, central nervous system, and peripheral nervous system.

In other embodiments, the biomarkers are neural proteins, peptides, fragments or derivatives thereof which are detected by an assay, as well as monoclonal antibodies and aptamers raised against the same. An in vitro diagnostic device is provided that further includes a process for determining the injury, disease, or repair of a subject or cells from the subject, that includes measuring a sample obtained from the subject or cells from the subject at a first time for a quantity of at least one biomarker which represents a biomarker sensitive/specific to the early phase of injury, disease, or repair; at least one biomarker sensitive/specific to an intermediate phase of injury, disease, or repair; and at least one biomarker sensitive/specific to the late phase of injury, disease, or repair. This is shown schematically in FIG. 1. These markers include illustratively include astroglia proteins such as glial fibrillary acidic protein (GFAP), S100 calcium-binding protein B (S100B), neuronal cell body protein visinin-like-1 (VILP-1), neuronal specific enolase (NSE), axonal degeneration proteins such as neurofilament protein-heavy (NF-H), neurofilament protein-medium (NF-M), neurofilament-light (NF-L), α-internexin (α-INT), synaptic damage marker synapsin isoforms (synapsin-1 and synapsin-2, synapsin-3, Synaptic vesicle glycoprotein 2A (SV2A), demyelination marker myelin basic protein (MBP), myelin oligodendrocyte glycoprotein (MOG), myelin associated glycoprotein (MAG) and proteolipid protein (PLP or lipophilin) and neurodegeneration markers such as total Tau (Tau), phosphorylated Tau (P-Tau) and (including phosphorylated epitopes at Thr181, Ser202, Ser205, Thr231, Ser396 and Ser-404), transactive response DNA binding protein 43 kDa (TDP-43), neuroinflammation-linked cytokine interleukin-6 (IL-6), and opsonization/phagocytosis-related proteins: complement protein C3, complement protein CR3, complement protein C4, complement protein C5, complement protein C1q, complement protein C3b, complement protein iC3b, C5b-9, C5aR, CD11b, TREM2, SIRPα, Nogo-66 receptor, DEC205, CX3CR1, CD68, CD45, and/or CD47.

It is appreciated that the aforementioned biomarkers have the attribute of being within detection limits of conventional detection techniques. In addition to the temporal combinatorial techniques, the present invention also provides techniques for enhancing Tau and P-Tau detection based on novel enhanced detection. The novel detection can be used as part of the present combinatorial invention or separate therefrom.

Through comparison of the quantity of each temporal phase biomarker of an inventive assay combination to normal levels for each such biomarker, the injury, disease, or repair of the subject is determined. An in vitro diagnostic device is also provided that necessarily incorporates an assay for determining the injury, disease, or repair of a subject or biological sample from the subject is also provided. The assay includes at least one biomarker in a biofluid, such as peripheral biofluid detectable in each of the injury, disease, or repair phases (early, intermediate, and late). In particular, while P-Tau protein is an attractive biomarker according to the present invention, detection limits have conventionally presented problems and in response to these problems a combination-based sandwich detection of a Tau protein is provided herein with a series of capture and detection antibody or aptamer pairs that are composed of a total Tau antibody or aptamer combined with Thr-181, Ser202, Thr-231, Ser-396/Ser-404 and Ser-409-specific antibodies within same detection unit. As a result, the simultaneous and combined detection of more molecules of Tau that are phosphorylated at multiple phosphorylation sites is provided, as compared to convention Tau detection techniques.

Alternatively, a sandwich detection approach for Tau relies on a series of capture and detection antibody or aptamer pairs based on a total Tau antibody or aptamer combined with a phospho-serine (P-Ser), phospho-threonine (P-Thr) and/or phospho-tyrosine (P-Tyr)-specific antibodies or aptamers. Thus, enabling the detection of more molecules of Tau that are phosphorylated at multiple phosphorylation sites in the same detection cell or unit. As a result, the simultaneous and combined detection of more molecules of Tau that are phosphorylated at multiple phosphorylation sites is provided, as compared to convention Tau detection techniques.

Still another alternative embodiment relies on a sandwich detection approach with a series of capture and detection antibody or aptamer pairs that is composed of a total Tau antibody or aptamer combined with a Pro-Ser and/or Pro-Thr specific antibodies or aptamers. Thus, enabling the detection of more molecules of Tau that are phosphorylated at multiple proline-directed phosphorylation sites in the same detection cell or unit. As a result, the simultaneous and combined detection of more molecules of Tau that are phosphorylated at multiple phosphorylation sites is provided, as compared to convention Tau detection techniques.

Still another alternative embodiment relies on a sandwich detection approach with a series of capture and detection antibody or aptamer pairs composed of the following two groups of antibody or aptamer: (A) a single P-Tau antibody or aptamer-based detection (from Thr-181, Ser202, Thr-231, Se-396/Ser-404 and Ser-409-specific antibodies or aptamers, combination-based use of multiple P-Tau-specific antibodies or aptamers (including Thr-181, Ser202, Thr-231, Se-396/Ser-404 and Ser-409-specific antibodies), and (B) CD61 as exosome surface marker, glutamate receptor (e.g. one of the NMDA receptor subunits, Glu receptor subunit or, metabotropic mGluR if MV originated from neurons, with Glu transporter as MV originated from astroglia, and/or CD11b, CD45, SIRPα and/or TREM2 as MV from microglia/macrophage.

A device also provides a process for determining if a subject has suffered mild, moderate, or severe TBI and/or disease in an event, which includes the aforementioned temporal biomarker assay, regardless of whether an enhanced Tau detection sandwich is present, for diagnosing different severities of injury, disease, or repair, as well as, distinguishing injury and/or disease types, such as determining whether a subject is suffering from TBI, stroke, subarachnoid hemorrhage, or other neuro injuries and/or diseases, thus by comparing the biomarker peak levels or trajectory of levels detected in a sample from the subject with a metric of what level is expected in a non-injured subject or the same subject at an earlier time point, using a scoring algorithm of an assay output and a pre-programmed comparison metric, which has been clinically validated, a device interpolates the data to determine if the subject has suffered an injury (TBI, stroke, SAH, etc.), determine the severity of injury (mild, moderate, severe) and critically the timing of the injury so as to predict the best treatment option(s) and a clinical outcome. A comparison of these biomarkers may also be used to determine other brain injury, neuro disease or neuro repair conditions using this or any number of additional biomarkers, such as neurotoxicity such as is disclosed in WO/2011/123844 and whose disclosure is incorporated herein by reference.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent +variability, any temperature, weight, volume, time interval, pH, salinity, molarity or molality, range, concentration and any other measurements, quantities or numerical expressions given herein are intended to be approximate and not exact or critical figures unless expressly stated to the contrary. Unless defined otherwise, all technical and scientific terms used herein have the same meaning as commonly understood by one of ordinary skill in the art.

As used herein, the term "subject in need thereof" refers to a mammal having a brain injury or suspected of having a brain injury, and includes human patients who have or are suspected of having physical trauma to the brain (e.g., mild, moderate or severe trauma, closed head injury, skull fracture, repeated trauma, and the like) and a disease or condition wherein damage to the brain is associated with or mediated by astroglial activation or astrogliosis (e.g., Alzheimer's disease, frontotemporal dementia (FTD), and other tauopathies and dementias. In particular, the conditions which a subject in need suffers from or is suspected of suffering from include, but are not limited to traumatic brain injury (TBI), chronic traumatic encephalopathy (CTE), Alzheimer's disease (AD), and frontotemporal dementia (FTD).

A biological sample is a biofluid in communication with the CNS or PNS of the subject prior to being isolated from the subject; for example, CSF, whole blood, plasma, serum, urine, sweat or saliva; and the agent is in each instance independently an antibody, aptamer, or other molecule that specifically binds at least one or more of the brain protein biomarker, regardless of whether the agent is for early, intermediate, or late phase injury, disease, or repair.

As used herein the term "diagnosing" means recognizing the presence or absence of a neurological, neurodegenerative or other condition including injury or disease or repair. Diagnosing is used in some instances herein referred to as the result of an assay wherein a particular combinatorial ratio, peak level or trajectory of a biomarker is detected or is absent.

As used herein a "ratio" is either a positive ratio wherein the level of the target is greater than the target in a second sample or relative to a known or recognized baseline level of the same target. A negative ratio describes the level of the target as lower than the target in a second sample or relative to a known or recognized baseline level of the same target. A neutral ratio describes no observed change in target biomarker.

As used herein a "neuro injury" is an alteration in cellular or molecular integrity, activity, level, robustness, state, or other alteration that is traceable to an event. Injury illustratively includes a physical, mechanical, chemical, biological, functional, infectious, or other modulator of cellular or molecular characteristics. An event is illustratively, a physical trauma such as an impact (percussive) or a biological abnormality such as a stroke resulting from either blockade or leakage of a blood vessel. An event is optionally an infection by an infectious agent, a change in treatment, or a disease relapse or remission. A person of skill in the art recognizes numerous equivalent events that are encompassed by the terms "injury", "disease" and "repair" from a reference point in time.

A neuro injury is optionally a physical event such as a percussive impact. An impact is the like of a percussive injury such as resulting to a blow to the head that either leaves the cranial structure intact or results in breach thereof. Experimentally, several impact methods are used illustratively including controlled cortical impact (CCI) at a 1.6 mm depression depth, equivalent to severe TBI in human. This method is described in detail by Cox, C D, et al., *J Neurotrauma,* 2008; 25 (11): 1355-65. It is appreciated that other experimental methods producing impact trauma are similarly operable.

As used herein, the term "brain injury" includes traumatic injuries and injuries as a result of disease, in particular neurodegenerative diseases and dementias. Thus, "brain injury" includes, but is not limited to mild, moderate, or severe trauma to the brain such as that received in military conflict, sports injury, accidents and falls, and the like, and also includes but is not limited to injury to the brain as a result of any tauopathy or dementia. In a specific embodiment, the brain injury is accompanied by, associated with, or mediated by astrogliosis or astroglial activation. Types of traumatic brain injury include closed or open head injuries, CTE, for example. Types of non-traumatic brain injury include tauopathy (a neurodegenerative disease associated with accumulation of Tau protein in neurofibrillary or gliofibrillary tangles in the brain, e.g., Alzheimer's disease, primary age-related tauopathy, CTE, frontotermporal dementia, Creutzfeldt-Jakob disease, forms of parkinsonianism, certain brain tumors, and the like).

As used herein, the term "astrogliosis," also referred to as "astrocytosis," "astroglial activation," or "reactive astrocytosis," refers to an increase in the number of astrocytes after destruction of neurons due to trauma, infection, ischemia, stroke, immune responses, neurodegenerative disease, or any cause. Astrogliosis also is accompanied by changes in astrocyte morphology and function. Astrogliosis is a pathologic abnormal increase in the number of astrocytes after destruction of nearby neurons due to trauma, infection, ischemia, autoimmune responses, or neurodegenerative disease such as Alzheimer's disease. Astroglial activation (reactive astrocytes) is a related phenomenon where the astrocytes in the area of an injury undergo changes in molecular expression and morphology as a response to physical or metabolic insult such as infection, ischemia, immune responses, inflammation, hemorrhage, trauma and the like. These cells can protect neurons by taking up toxins from the area and repairing the blood brain barrier, but also can have negative effects that prevent axon regeneration and produce scar tissue.

As used herein, the term "GFAP" refers to intact glial fibrillary acidic protein, an intermediate filament protein encoded by the GFAP gene in humans and expressed in the central nervous system, primarily in astrocytes. All isoforms of the GFAP protein are included in this definition. As used herein, the term also refers to breakdown products of GFAP, including natural and synthetic peptides derived from the sequence of GFAP. Therefore, "GFAP or a fragment thereof" refers to full length GFAP isoforms or any breakdown product, for example, the central core breakdown product GFAP-38K (with residue range about 79-383 in GFAP-α), the N-terminal head region with residue range about 1-72 in GFAP-α, and the C-terminal tail region with residue range about 378-432 in GFAP-α, i.e., the truncated forms of GFAP with apparent molecular weights of about 44 kDa, 42 kDa, 40 kDa and 38 kDa.

Glial fibrillary acidic protein (GFAP) is a structural protein unique to astrocytes. GFAP is a component in the cytoskeletal structure of astroglial cells and operates in maintaining their mechanical strength, as well as supporting neighboring neurons and the blood-brain barrier (BBB). Because GFAP is enriched in astroglial cells in the CNS, it can be used as a biomarker for diagnosis or prognosis of TBI. Shortly following TBI, there is a release of high concentration of GFAP (intact protein, 50 kDa) and its fragments (peptides, also known as breakdown products (BDPs), 38 kDa-44 kDa) from astrocytes into the extracellular fluid and cerebrospinal fluid and blood.

Therefore, GFAP is a pathological hallmark of astrogliosis in TBI pathology. An increase in GFAP is believed to be an indicator of the astroglial activation and hypertrophy observed following brain injury. Activated astrocytes are known to mediate the neuroinflammation process, including the release for proinflammatory cytokines (e.g. IL-6, TNF-alpha). Activated astroglia cells also form the so-called glial scar that can further inhibit neuroregeneration. After TBI and rupture of the BBB, GFAP is released from damaged astrocytes, enters the bloodstream where it can trigger an immune response in a subset of TBI patients. Therefore, in some TBI patients, there is a blood-based dominant autoantibody response to GFAP protein apparent after injury. Currently, it is not known if astroglial cell activation is beneficial or detrimental to recovery from TBI, however it may be both. Neuroinflammation initially can be beneficial by removing cell and neurotoxic debris from the site of injury, but sustained and unresolved neuroinflammation can be harmful.

As used herein, the term "immunization" refers to any passive or active method of introducing or producing antibodies specific to a particular antigen. For example, immunization for GFAP includes administration of antibodies that specifically recognize GFAP or an epitope or hapten of GFAP to a subject, or an aptamer that binds to GFAP; such types of immunization relate to a passive immunization. Immunization also includes administration of GFAP protein or a peptide derived from GFAP to the subject in order to stimulate the immune system of the subject to produce antibodies that specifically recognize GFAP, an active immunization. Both active and passive immunization is included in the term "immunization" and all of its cognates, unless stated otherwise.

As used herein, the term "GFAP antibody ("anti-GFAP antibody") or a fragment thereof" refers to an intact anti-GFAP antibody or a combination of fragmented heavy and light chains of immunoglobulin or single chain fusion protein containing heavy-light chain plus light brain variable fragments. Any type of antibody is included within the term if it specifically binds to GFAP or a fragment or breakdown product of GFAP. As used herein, the term "GFAP aptamer" refers to one or more single-stranded oligonucleotide (DNA or RNA) molecules that bind to a specific target molecule, e.g., GFAP or a fragment thereof.

As used herein, the term "therapeutically effective amount" refers to an amount of a compound or composition that, when administered to a subject for treating a disease or disorder, or at least one of the clinical symptoms of a disease or disorder, is sufficient to affect such disease, disorder, or symptom. A "therapeutically effective amount" includes an amount that ameliorates, reduces or cures the disease, disorder, or symptom and may vary depending, for example, on the compound, the disease, disorder, and/or symptoms of the disease or disorder, severity of the disease, disorder, and/or symptoms of the disease or disorder, the age, weight, and/or health of the subject to be treated, the capacity of the individual's immune system to synthesize antibodies, the degree of protection desired, the formulation of the vaccine, the treating doctor's assessment of the medical situation, and other relevant factors. A therapeutically effective amount can be a single dose or a series of doses administered to a subject in need thereof. An appropriate amount in any given instance may be readily ascertained by those skilled in the art or can be determined by routine experimentation.

The present invention provides for the detection of injury, disease, or repair in a subject. An injury, disease, or repair may be an abnormal injury, disease, or repair such as that caused by genetic disorder, injury, or disease to nervous tissue. As such, it is a further object of the present invention to provide a means for detecting or diagnosing an abnormal injury, disease, or repair in a subject.

The present invention also provides an assay for detecting or diagnosing the injury, disease, or repair of a subject. As the injury, disease, or repair may be the result of stress such as that from exposure to environmental, therapeutic, or investigative compounds, it is a further aspect of the present invention to provide a process and assay for screening candidate drugs or other compounds or for detecting the effects of environmental contaminants regardless of whether the subject itself or cells derived there from are exposed to the drug candidate or other possible stressors.

The present invention also provides clinical treatment with precision medicines for the same therapeutic targets as a subset of the temporal biomarkers. If the clinical treatment is with a precision medicine for at least one of the same therapeutic targets as a subset of the temporal biomarkers and involves opsonization, stabilization or destabilization, binding, and/or accelerated clearance or phagocytosis of brain debris or decelerated generation of brain debris, then accelerated clearance of these proteins and other temporal biomarkers described herein are then reflected by modulated levels in the blood/CSF/lymphatic fluid and/or inversely modulated levels in the brain.

FIG. 1 schematically illustrates precision medicine usage based on the inventive combinatorial temporal biomarkers because the precision medicines described herein target the type, phase and amplitude (severity) of the injury, disease, or repair that are determined with the combinatorial temporal biomarker measurements described herein. An inventive precision medicine to accelerate repair and/or improve cognition leverages the kinetic windows provided by the combinatorial temporal biomarker readouts described herein to improve safety, efficacy and therapeutic index. Likewise, an inventive precision medicine leverages synergistic effects provided by the combinatorial temporal biomarker readouts described herein to improve safety, efficacy and therapeutic index. Lastly, an inventive precision medicine targets at least one of the same therapeutic targets as a subset of the temporal biomarkers described herein.

In Vitro Diagnostic Device

Figure 2:
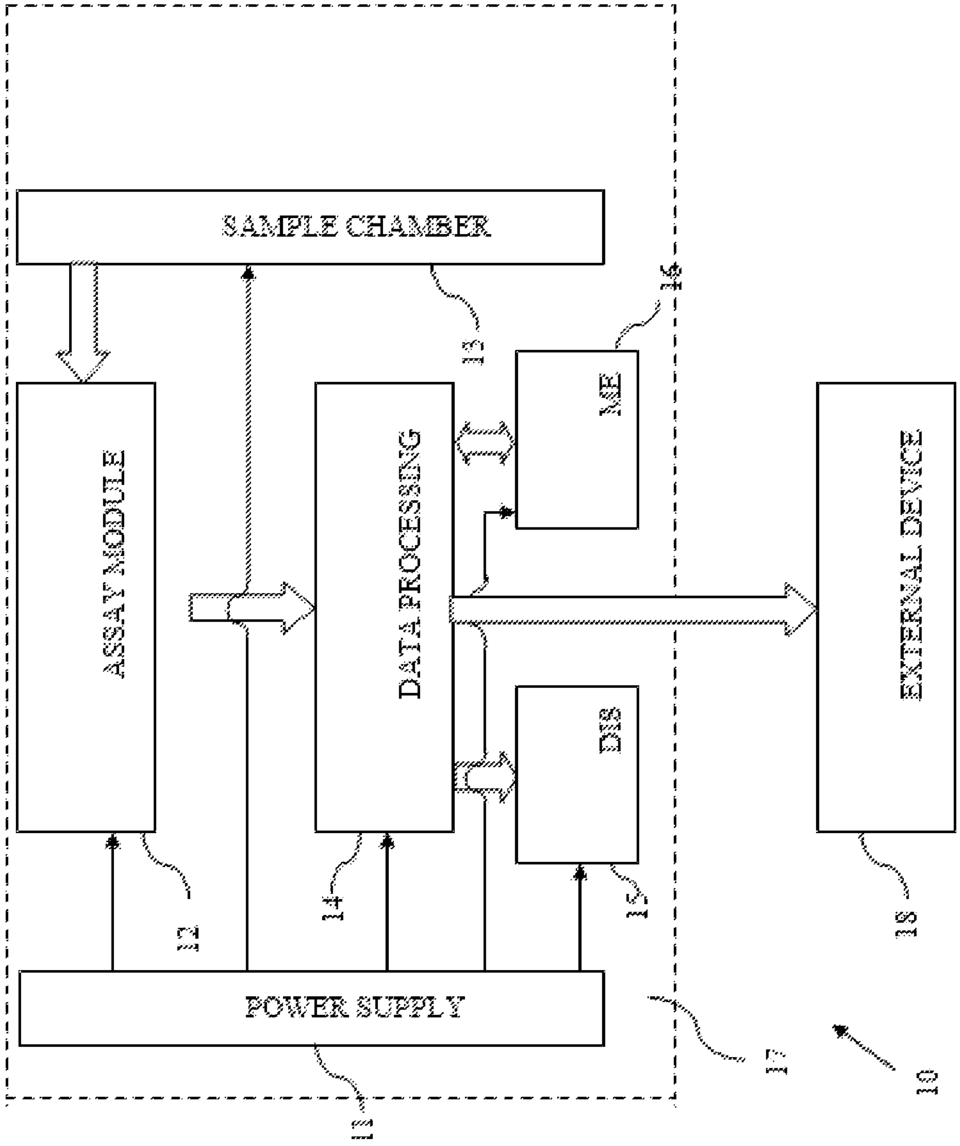
FIG. 2 is a schematic of an inventive in vitro diagnostic device.

FIG. 2 schematically illustrates an inventive in vitro diagnostic device shown generally at 10. An inventive in vitro diagnostic device includes at least a sample collection chamber 13, an assay module 12 used to detect biomarkers of injury, disease or repair, and a user interface that relates the concentration (level) of the measured biomarker measured in the assay module. The in vitro diagnostic device may be a handheld device, a bench top device, or a point of care device.

The sample chamber 13 can be of any sample collection apparatus known in the art for holding a biological fluid. In one embodiment, the sample collection chamber can accommodate any one of the biological fluids herein contemplated, such as whole blood, plasma, serum, urine, sweat or saliva.

The assay module 12 is preferably made of an assay which may be used for detecting a protein antigen in a biological sample, for instance, through the use of antibodies in an immunoassay. The assay module 12 may include any assay currently known in the art; however, the assay should be optimized for the detection of temporal biomarkers used for detecting injury, disease or repair in a subject. The assay module 12 is in fluid communication with the sample collection chamber 13. In one embodiment, the assay module 12 includes of an immunoassay where the immunoassay may be any one of a radioimmunoassay, ELISA (enzyme linked immunosorbent assay), "sandwich" immunoassay, immunoprecipitation assay, precipitin reactions, gel diffusion precipitin reactions, immunodiffusion assay, fluorescent immunoassay, chemiluminescent immunoassay, phosphorescent immunoassay, or an anodic stripping voltammetry immunoassay. In one embodiment a colorimetric assay may be used which may include only of a sample collection chamber 13 and an assay module 12 of the assay. Although not specifically shown these components are preferably housed in one assembly 17.

In one embodiment, the inventive in vitro diagnostic device contains a power supply 11, an assay module 12, a sample chamber 13, and a data processing module 14. The power supply 11 is electrically connected to the assay module and the data processing module 14. The assay module 12 and the data processing module 14 are in electrical communication with each other. As described above, the assay module 12 may include any assay currently known in the art; however, the assay should be optimized for the detection of the biomarkers used herein for detecting injury disease, or repair in a subject. The assay module 12 is in fluid communication with the sample collection chamber 13. The assay module 12 includes of an immunoassay where the immunoassay may be any one of a radioimmunoassay, ELISA (enzyme linked immunosorbent assay), "sandwich" immunoassay, immunoprecipitation assay, precipitin reactions, gel diffusion precipitin reactions, immunodiffusion assay, fluorescent immunoassay, chemiluminescent immunoassay, phosphorescent immunoassay, or an anodic stripping voltammetry immunoassay. A biological sample is placed in the sample chamber 13 and assayed by the assay module 12 detecting for a biomarker of injury, disease, or repair. The measured amount of the biomarker by the assay module 12 is then electrically communicated to the data processing module 14. The data processing 14 module may include any known data processing element known in the art, and may include a chip, a central processing unit (CPU), or a software package which processes the information supplied from the assay module 12.

In one embodiment, the data processing module 14 is in electrical communication with a display 15, a memory device 16, or an external device 18 or software package [such as laboratory and information management software (LIMS)]. In one embodiment, the data processing module 14 is used to process the data into a user defined usable format. This format includes the measured concentration (levels) of temporal biomarkers detected in the sample, indication that an injury, disease, or repair is present, or indication of the severity of the injury, disease, or repair. The information from the data processing module 14 may be illustrated on the display 15, saved in machine readable format to a memory device, or electrically communicated to an external device 18 for additional processing or display. Although not specifically shown these components are preferably housed in one assembly 17. In one embodiment, the data processing module 14 may be programmed to compare the detected amount of the biomarker transmitted from the assay module 12, to a comparator algorithm. The comparator algorithm may compare the measured amount to the user defined threshold which may be any limit useful by the user. In one embodiment, the user defined threshold is set to the amount of the biomarker measured in control subject, or a statistically significant average of a control population.

In one embodiment, an in vitro diagnostic device may include one or more devices, tools, and equipment configured to hold or collect a biological sample from an individual. In one embodiment of an in vitro diagnostic device, tools to collect a biological sample may include one or more of a swab, a scalpel, a syringe, a scraper, a container, and other devices and reagents designed to facilitate the collection, storage, and transport of a biological sample. In one embodiment, an in vitro diagnostic test may include reagents or solutions for collecting, stabilizing, storing, and processing a biological sample. These reagents include antibodies, aptamers, or combinations thereof raised against one of the aforementioned biomarkers. In one embodiment, an in vitro diagnostic device, as disclosed herein, may include a micro array apparatus and reagents, and additional hardware and software necessary to assay a sample to detect and visualize the temporally relevant biomarkers.

Kits

In yet another aspect, the invention provides kits for aiding a diagnosis of injury, disease, or repair, including type, phase amplitude (severity), subcellular localization, wherein the kits may be used to detect the markers of the present invention. For example, the kits can be used to detect any one or more of the biomarkers described herein, which markers are differentially present in samples of a patient and normal subjects. The kits of the invention have many applications. For example, the kits may be used to differentiate if a subject has axonal injury versus, for example, dendritic, or has a negative diagnosis, thus aiding injury, disease, or repair diagnosis. In another example, the kits can be used to identify compounds that modulate expression of one or more of the markers in in vitro or in vivo animal models to determine the effects of treatment.

In one embodiment, a kit includes (a) an antibody that specifically binds to an aforementioned marker; and (b) a detection reagent. Such kits are prepared from the materials described above, and the previous discussion regarding the materials (e.g., antibodies, aptamers detection reagents, immobilized supports, etc.) being fully applicable to this section and thus is not repeated.

In one inventive embodiment, the kit includes (a) a panel or composition of detecting agent to detect a panel or composition of biomarkers. The panel or composition of reagents included in a kit provide for the ability to detect at least one each of the early, intermediate, and late biomarkers in order to diagnose an injury, disease or repair event. These biomarkers corresponding to at least one each of early, intermediate, and late phases of the injury, disease or repair process as detailed in Table 1 as shown below in example 3.

In one embodiment, the invention includes a diagnostic kit for use in screening serum containing antigens of the biomarkers of the invention. The diagnostic kit in this embodiment includes a substantially isolated antibody or aptamer specifically immunoreactive with peptide or polynucleotide antigens, and visually detectable labels associated with the binding of the polynucleotide or peptide antigen to the antibody or aptamer. In one embodiment, the antibody or aptamer is attached to a solid support. Antibodies or aptamers used in the inventive kit are those raised against any one of the biomarkers used herein for temporal data. In one embodiment, the antibody is a monoclonal or polyclonal antibody or aptamer raised against the rat, rabbit or human forms of the biomarker. The detection reagent of the kit includes a second, labeled monoclonal or polyclonal antibody or aptamer. Alternatively, or in addition thereto, the detection reagent includes a labeled, competing antigen.

In one diagnostic configuration, test serum is reacted with a solid phase reagent having a surface-bound antigen obtained by the methods of the present invention. After binding with specific antigen antibody or aptamer to the reagent and removing unbound serum components by washing, the reagent is reacted with reporter-labeled anti-human antibody or aptamer to bind reporter to the reagent in proportion to the amount of bound anti-antigen antibody or aptamer on the solid support. The reagent is again washed to remove unbound labeled antibody or aptamer, and the amount of reporter associated with the reagent is determined. Typically, the reporter is an enzyme which is detected by incubating the solid phase in the presence of a suitable fluorometric, luminescent or colorimetric substrate.

The solid surface reagent in the above assay is prepared by known techniques for attaching protein or oligonucleotide material to solid support material, such as polymeric beads, dip sticks, 96-well plate or filter material. These attachment methods generally include non-specific adsorption of the protein oligonucleotide to the support or covalent attachment of the protein or oligonucleotide, typically through a free amine group, to a chemically reactive group on the solid support, such as an activated carboxyl, hydroxyl, or aldehyde group. Alternatively, streptavidin coated plates can be used in conjunction with biotinylated antigen(s).

In some embodiments, the kit may include a standard or control information so that the test sample can be compared with the control information standard to determine if the test amount of a marker detected in a sample is a diagnostic amount consistent with a diagnosis of injury, disease, or repair, including type, phase, amplitude (severity), subcellular localization, brain disorder and/or effect of treatment on the patient.

In one embodiment, a kit includes: (a) a substrate including an adsorbent thereon, wherein the adsorbent is suitable for binding a marker, and (b) instructions to detect the marker or markers by contacting a sample with the adsorbent and detecting the marker or markers retained by the adsorbent. In some embodiments, the kit may include an eluant (as an alternative or in combination with instructions) or instructions for making an eluant, wherein the combination of the adsorbent and the eluant allows detection of the markers using gas phase ion spectrometry. Such kits can be prepared from the materials described above, and the previous discussion of these materials (e.g., probe substrates, adsorbents, washing solutions, etc.) is fully applicable to this section and will not be repeated.

In certain embodiments, the kit further includes instructions for suitable operational parameters in the form of a label or a separate insert. For example, the kit may have standard instructions informing a consumer how to wash the probe after a sample is contacted on the probe. In another example, the kit may have instructions for pre-fractionating a sample to reduce complexity of proteins in the sample. In another example, the kit may have instructions for automating the fractionation or other processes.

Biofluids

The inventive method and in vitro diagnostic devices provide the ability to detect and monitor levels of those temporal protein biomarkers or autoantibodies thereto which are released into the body after neurotoxicity or CNS or PNS injury, disease, or repair to provide enhanced diagnostic capability by allowing clinicians (1) to determine the type, phase and amplitude (severity) of injury or disease or repair in various patients, (2) to monitor patients for signs of secondary CNS or PNS injuries, diseases or repairs that may elicit these cellular changes and (3) to continually monitor the progress of the injury, disease, or repair and the effects of therapy by examination of these temporal biomarkers in biological fluids (synonymously referred to herein as "biofluids"), such as blood, plasma, serum, CSF, urine, saliva or sweat. Unlike other organ-based diseases where rapid diagnostics by surrogate biomarkers prove invaluable to the course of action taken to treat the disease, no such rapid, definitive diagnostic tests exist for injury, disease, or repair states such as traumatic or ischemic injury that might provide physicians with quantifiable temporal biomarkers to help determine the degree of the injury, disease or repair; the anatomical and cellular pathology of the injury, disease or repair; and the implementation of appropriate medical management and treatment.

A biological sample operative herein includes cells, tissues, cerebral spinal fluid (CSF), whole blood, serum, plasma, cytosolic fluid, urine, feces, stomach fluids, digestive fluids, saliva, nasal or other airway fluid, vaginal fluids, semen, or other biological fluid recognized in the art. It should be appreciated that after injury or disease of the CNS or PNS (such as TBI), the neural cell membrane is compromised, leading to the efflux of neural proteins first into the extracellular fluid, and to the cerebrospinal fluid. Eventually the neural proteins efflux to the circulating blood (as assisted by the compromised blood brain barrier for brain injuries or diseases) and, through normal bodily function (such as impurity removal from the kidneys), the neural proteins migrate to other biological fluids such as urine, sweat, and saliva. Thus, other suitable biological samples include, but are not limited to such cells or fluid secreted from these cells. It should also be appreciated that obtaining biological fluids such as cerebrospinal fluid, blood, plasma, serum, saliva, and urine, from a subject is typically much less invasive and traumatizing than obtaining a solid tissue biopsy sample. Thus, biofluids, are preferred for use in the invention.

Biological samples of CSF, blood, urine, and saliva are collected using normal collection techniques. For example, and not to limit the sample collection to the procedures contained herein, CSF Lumbar Puncture (LP) a 20-gauge introducer needle is inserted, and an amount of CSF is withdrawn. For blood, the samples may be collected by venipuncture in Vacutainer tubes and being amenable to being spun down and separated into serum and plasma. For urine and saliva, samples that are collected avoiding the introduction of contaminants into the specimen are preferred. All biological samples may be stored in aliquots at −80° C. for later assay. Surgical techniques for obtaining solid tissue samples are well known in the art. For example, methods for obtaining a nervous system tissue sample are described in standard neuro-surgery texts such as Atlas of Neurosurgery: Basic Approaches to Cranial and Vascular Procedures, by F. Meyer, Churchill Livingstone, 1999; Stereotactic and Image Directed Surgery of Brain Tumors, 1st ed., by David G. T. Thomas, WB Saunders Co., 1993; and Cranial Microsurgery: Approaches and Techniques, by L. N. Sekhar and E. De Oliveira, 1st ed., Thieme Medical Publishing, 1999. Methods for obtaining and analyzing brain tissue are also described in Belay et al., Arch. Neurol. 58:1673-1678 (2001); and Seijo et al., J. Clin. Microbiol. 38:3892-3895 (2000). Any suitable biological samples can be obtained from a subject to detect markers. It should be appreciated that the methods employed herein may be identically reproduced for any biological fluid to detect a marker or markers in a sample.

After insult, the damaged tissue, organs, or nerve cells in in vitro culture or in situ in a subject express altered levels or activities of one or more proteins than do such cells not subjected to the insult. Thus, samples that contain nerve cells, e.g., a biopsy of CNS or PNS tissue are illustratively suitable biological samples for use in the invention.

A subject illustratively includes a dog, a cat, a horse, a cow, a pig, a sheep, a goat, a chicken, non-human primate, a human, a rat, and a mouse. Subjects who most benefit from the present invention are those suspected of having or at risk for developing abnormal injury, disease, or repair, such as victims of the injuries or diseases such as those aforementioned herein.

Baseline levels of several biomarkers are those levels obtained in the target biological sample in the species of desired subject in the absence of a known injury, disease, or repair. These levels need not be expressed in hard concentrations but may instead be known from parallel control experiments and expressed in terms of fluorescent units, density units, and the like. Typically, baselines are determined from subjects where there is an absence of a biomarker or present in biological samples at a negligible amount. However, some proteins may be expressed less in an injured, diseased or repaired patient or before any clinical measures of injury, disease, or repair. Determining the baseline levels of protein biomarkers in a particular species is well within the skill of the art.

To provide correlations between an injury, disease, or repair and measured quantities of the temporal biomarkers, biological samples are collected from subjects in need of measurement for these biomarkers to assess injury, disease, or repair. Detected levels of a given temporal biomarker are optionally correlated with CT scan results as well as GCS scoring.

The detection methods may be implemented into assays or into kits for performing assays. These kits or assays may alternatively be packaged into a cartridge to be used with an inventive in vitro diagnostic device. Such a device makes use of these cartridges, kits, or assay in an assay module 12, which may be one of many types of assays. The biomarkers of the invention can be detected in a sample by a variety of conventional methods. For example, immunoassays, include but are not limited to competitive and non-competitive assay systems using techniques such as western blots, radioimmunoassays, ELISA (enzyme linked immunosorbent assay), "sandwich" immunoassays, magnetic immunoassays, radioisotope immunoassay, fluorescent immunoassays, immunoprecipitation assays, precipitin reactions, gel diffusion precipitin reactions, immunodiffusion assays, fluorescent immunoassays, chemiluminescent immunoassays, phosphorescent immunoassays, anodic stripping voltammetry immunoassay, and the like. Inventive in vitro diagnostic devices may also include any known devices currently available that utilize ion-selective electrode potentiometry, microfluids technology, fluorescence or chemiluminescence, or reflection technology that optically interprets color changes on a protein test strip. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation). It should be appreciated, that at present, none of the existing technologies present a method of detecting or measuring any of the ailments disclosed herein, nor does there exist any methods of using such in vitro diagnostic devices to detect any of the disclosed biomarkers to detect their associated injuries.

An exemplary process for detecting the presence or absence of a biomarker, alone or in combination, in a biological sample involves obtaining a biological sample from a subject, such as a human, contacting the biological sample with a compound or an agent capable of detecting of the marker being analyzed, illustratively including an antibody or aptamer, and analyzing binding of the compound or agent to the sample after washing. Those samples having specifically bound compound or agent express the marker being analyzed.

For example, in vitro techniques for detection of a marker illustratively include enzyme linked immunosorbent assays (ELISAs), radioimmunoassay, radioassay, western blot, Southern blot, northern blot, immunoprecipitation, immunofluorescence, mass spectrometry, RT-PCR, PCR, liquid chromatography, high performance liquid chromatography, enzyme activity assay, cellular assay, positron emission tomography, mass spectroscopy, combinations thereof, or other technique known in the art. Furthermore, in vivo techniques for detection of a marker include introducing a labeled agent that specifically binds the marker into a biological sample or test subject. For example, the agent can be labeled with a radioactive marker whose presence and location in a biological sample or test subject can be detected by standard imaging techniques. In some inventive embodiments a first temporal biomarker early, intermediate, and late specific binding agent and other agents specifically binding at least one additional temporal biomarker are bound to a substrate. It is appreciated that a bound agent assay is readily formed with the agents bound with spatial overlap, with detection occurring through discernibly different detection of each temporal biomarkers. A color intensity-based quantification of each of the spatially overlapping bound biomarkers is representative of such techniques.

A preferred agent for detecting a temporal biomarker is an antibody or aptamer capable of binding to the biomarker being analyzed. More preferably, the antibody or aptamer is conjugated with a detectable label. Such antibodies can be polyclonal or monoclonal. An intact antibody, a fragment thereof (e.g., Fab or F(ab') 2), or an engineered variant thereof (e.g., sFv) or an aptamer or bi-/tri-specific aptamer can also be used. Such antibodies can be of any immunoglobulin class including IgG, IgM, IgE, IgA, IgD and any subclass thereof. Antibodies and aptamers for numerous inventive biomarkers are available from vendors known to one of skill in the art. Exemplary antibodies operative herein are used to detect a biomarker of the disclosed conditions. In addition, antigens to detect autoantibodies may also be used to detect late injury of the stated injuries and disorders.

An antibody or aptamer is labeled in some inventive embodiments. A person of ordinary skill in the art recognizes numerous labels operable herein. Labels illustratively include, fluorescent labels, biotin, peroxidase, radionucleotides, or other label known in the art. Alternatively, a detection species of another antibody or aptamer or other compound known to the art is used as form detection of a biomarker bound by an antibody or aptamer.

Antibody- and aptamer-based assays operative herein include western blotting immunosorbent assays (e.g., ELISA and RIA) and immunoprecipitation assays. As one example, the biological sample or a portion thereof is immobilized on a substrate, such as a membrane made of nitrocellulose or PVDF; or a rigid substrate made of polystyrene or other plastic polymer such as a microtiter plate, and the substrate is contacted with an antibody or aptamer that specifically binds a temporal biomarker under conditions that allow binding of antibody or aptamer to the biomarker being analyzed. After washing, the presence of the antibody or aptamer on the substrate indicates that the sample contained the marker being assessed. If the antibody or aptamer is directly conjugated with a detectable label, such as an enzyme, fluorophore, or radioisotope, the presence of the label is optionally detected by examining the substrate for the detectable label. Alternatively, a detectably labeled secondary antibody or aptamer that binds the marker-specific antibody or aptamer is added to the substrate. The presence of detectable label on the substrate after washing indicates that the sample contained the biomarker.

Numerous permutations of these basic immunoassays are also operative in the invention. These include the biomarker-specific antibody or aptamer, as opposed to the sample being immobilized on a substrate, and the substrate is contacted with a biomarker conjugated with a detectable label under conditions that cause binding of antibody or aptamer to the labeled marker. The substrate is then contacted with a sample under conditions that allow binding of the marker being analyzed to the antibody or aptamer. A reduction in the amount of detectable label on the substrate after washing indicates that the sample contained the marker.

Although antibodies or aptamers are preferred for use in the invention because of their extensive characterization, any other suitable agent (e.g., a peptide or a small organic molecule) that specifically binds a biomarker is operative herein in place of the antibody or aptamer in the above described immunoassays. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

A myriad of detectable labels that are operative in a diagnostic assay for biomarker expression are known in the art. Agents used in methods for detecting a biomarker are conjugated to a detectable label, e.g., an enzyme such as horseradish peroxidase. Agents labeled with horseradish peroxidase may be detected by adding an appropriate substrate that produces a color change in the presence of horseradish peroxidase. Several other detectable labels that may be used are known. Common examples of these detectable labels include alkaline phosphatase, horseradish peroxidase, fluorescent compounds, luminescent compounds, colloidal gold, magnetic particles, biotin, radioisotopes, and other enzymes. It is appreciated that a primary/secondary antibody or aptamer system is optionally used to detect one or more biomarkers. A primary antibody or aptamer that specifically recognizes one or more biomarkers is exposed to a biological sample that may contain the biomarker of interest. A secondary antibody or aptamer with an appropriate label that recognizes the species or isotype of the primary antibody or aptamer is then contacted with the sample such that specific detection of the one or more biomarkers in the sample is achieved.

The present invention provides a step of comparing the quantity of one or more temporal biomarkers to normal levels to determine the injury, disease, or repair of the subject. It is appreciated that selection of the temporal biomarkers or even additional biomarkers allows one to identify the types of cells implicated in an abnormal organ or physical condition as well as the nature of cell death in the case of an axonal injury marker. The practice of an inventive process provides a test which can help a physician determine suitable therapeutics to administer for optimal benefit of the subject. While the neural data provided in the examples herein are provided with respect to a full spectrum of TBI, neurotoxicity, and neuronal cell death, it is appreciated that these results are applicable to other aforementioned forms of injury, disease, or repair. As is shown in the subsequently provided example data, a gender difference is unexpectedly noted in abnormal subject injury, disease, or repair.

The results of such a test using an in vitro diagnostic device can help a physician determine whether the administration of a particular therapeutic or treatment regimen may be effective and provide a rapid clinical intervention to the injury or disorder to enhance a patient's recovery.

It is appreciated that other reagents such as assay grade water, buffering agents, membranes, assay plates, secondary antibodies or aptamers, salts, and other ancillary reagents are available from vendors known to those of skill in the art.

Methods involving conventional biological techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Treatment with Precision Medicines

The temporal biomarkers used herein as the one or more early, intermediate, and late biomarkers as a diagnostic or prognostic are also amenable as therapeutic targets for precision medicines for neuro injury, neuro disease, or neuro repair, including therapeutic feedback loops to guide treatment or adaptive clinical trials, as detailed above with respect to FIG. 1. By way of example, biomarkers that are amenable to targeting to treatment negative consequences associated with the presence of the biomarker, such as systemic inflammatory response syndrome. Therapeutic targets amendable to precision medicine targeting illustratively include GFAP, Tau, P-Tau, SV2A, SYN-1/-2/-3, EIF2alpha, EIF2beta, and combinations thereof. It is appreciated that some of these targets are not only associated with a biomarker used herein but are themselves biomarkers operative in the present invention. Exemplary biomarker pairs particularly well-suited for usage with precision medicine targeting illustratively include S100B and NSE, GFAP and UCH-L1, Tau and P-Tau. Conditions that can benefit from such treatment include a variety of neuro injuries, neuro diseases, and neuro repair that include mild traumatic brain injury, complicated mild traumatic brain injury, moderate traumatic brain injury, severe traumatic brain injury, vanishing white matter disease, multiple sclerosis, stroke, epilepsy, Alzheimer's disease, chronic traumatic encephalopathy, and tauopathy.

Precision treatments are administered by routine techniques for each such medicine. Such techniques include intravenous, intrathecal, intramuscular, and oral routes. Exemplary precision medications operative herein include an anti-GFAP monoclonal antibody or aptamer, an anti-Tau antibody or aptamer, a transferrin-receptor targeting component, levetiracetam, and a combination thereof, including antibody- or aptamer-drug conjugates and bispecifics.

EXAMPLES

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to mammalian tissue, specifically, analyses of mouse tissue, a person having ordinary skill in the art recognizes that similar techniques and other techniques known in the art readily translate the examples to other mammals such as humans. Reagents illustrated herein are commonly cross reactive between mammalian species or alternative reagents with comparable properties, are commercially available, and a person of ordinary skill in the art readily understands where such reagents may be obtained. Variations within the concepts of the invention are apparent to those skilled in the art.

Example 1

Mild traumatic brain injury (mTBI) subjects/patients are tested for early-, intermediate- and late-combinatorial precision biomarkers (e.g., glial fibrillary acidic protein (GFAP), phospho-Tau protein (P-Tau) and total Tau (Tau) with combinatorial antibody or aptamer-based detection methods to determine if they are predicted to progress to complicated mTBI (aka, mTBI with persistent concussive symptoms) based on previous datasets. The subset of patients identified to have significant levels of early predictive biomarkers (e.g., GFAP) for progression to complicated mTBI (i.e., the enriched subjects/patients) are selected for treatment with a therapeutic agent (e.g., a therapeutic antibody, aptamer, bispecific, antibody drug conjugate, or small molecule) to block progression to complicated mTBI (or mTBI with persistent symptoms such as cognitive/memory dysfunction, lack of concentration, anxiety, headache, dizziness, and sleep disturbance), accelerate brain repair, and/or improve cognition. Treatment response is monitored with combinatorial antibody or aptamer-based detection methods to determine if levels of intermediate- or long-lived biomarkers (e.g., P-Tau/Tau) are significantly modulated by the treatment, thus serving as surrogate or monitoring endpoints for safety, efficacy and cognitive improvement. If the clinical treatment is with a precision medicine (e.g., an anti-GFAP or -Tau or P-Tau- or Syn-1, -2, -3 or -SV2A monoclonal antibody or aptamer or small molecule) for at least one of the same therapeutic targets as a subset of the temporal biomarkers (e.g. GFAP, Tau, P-Tau, Syn-1/-2/-3 or SV2A, and other intracellular proteins, as well as their breakdown products, in the extracellular space) and involves opsonization, stabilization or destabilization, binding, and/or accelerated clearance or phagocytosis of brain debris or decelerated generation of brain debris, then accelerated clearance of these proteins and other temporal biomarkers described herein are then reflected by modulated levels in the blood/CSF/lymphatic fluid and/or inversely modulated levels in the brain, thus serving as a pharmacodynamic/response biomarker too.

Example 2

Protein biomarker release is not uniform, thus the temporal profile of individual injury, disease, or repair biomarker protein in biofluid-(such as blood or CSF) injury, disease, or repair varies.

In the case of injury (e.g. TBI, spinal cord injury, stroke, cerebral hemorrhage), there is a point in time when the injury event occurs. Thus, all the time points following this injury event can be referenced to as post-event such as post injury plus: day 1, day 2, day 10, 1-month, 3-month, 12 months. In the case of disease or repair, there is a point in time when the disease or repair is observed clinically such as the relapse or remission of a multiple sclerosis (MS) patient. Thus, all the time points before and after this clinical event can be referenced to as pre- and post-disease or repair, respectively.

The blood levels of these biomarkers can be characterized as three phases: early phase (within the first 48 h) post-event, intermediate phase (>48 h to 10 days) post-event, and late phase (>10 days to months) post-event. FIG. 1 schematically shows the post-injury,-disease activity or -repair temporal biomarker concentration profiles in blood and the combinatory biomarker levels over time (albeit pre-injury, -disease and -repair measurements from the reference point of the event, or pre-events, are also described herein). By using the inventive combinatorial levels approach for these three phases, one combines levels of one of: early, intermediate, and late biomarkers, thus achieving a sustained and detectable overall injury, disease, or repair activity and repair signals in blood over the early, intermediate, and late phases post-injury.

Example 3

Markers readily detectable and/or have the highest levels in a biological sample such as blood within this early phase (within the first 48 hours post-event) include GFAP, visinin-like protein-1 (VILP-1), NSE and S100B, glutamate decarboxylases 1 and 2 (GAD1, GAD2, respectively). The biological sample levels of this subset of early biomarkers with the first 48 hours post-event is particularly useful in the prognosing patient's outcome. (i.e., elevated levels of injury or disease markers in the early phase predicts poor patient outcome while elevated levels of repair markers predict good patient outcome and vice versa).

Markers readily detected and/or have the highest levels in biofluid such as blood within the intermediate phase (>48 h to 10 days post-event) include α-internexin (aa-INT), neurofilament proteins NF-H, NF-M, NF-L, synapsin isoforms, myelin basic protein (MBP), myelin oligodendrocyte glycoprotein (MOG), synapsin-1/-2/-3, myelin oligodendrocyte associated protein (MAG), proteolipid protein (PLP), SV2A, complement C3, complement C4, complement C5, complement C1q, complement protein iC3b, C5b-9, C5aR, and CD11b, TREM2, SIRPα, Nogo-66 receptor, DEC205, C3CXR1, CD68, CD45, or CD47. The biofluid levels of this set of biomarkers >48 h to 10 days post-event is particularly useful in monitoring delayed axonal demyelination/remyelination or synaptic damage/repair as a result of an early injury, disease, or repair event, respectively.

These intermediate markers might also be highly responsive to therapeutic treatment for injury, disease, or repair that serves to attenuate such intermediate injury, disease, or repair associated events (e.g., axonal injury, demyelination and/or synaptic damage).

Markers readily detected and/or have the highest levels in biofluid such as blood within the late phase (>10 days to months post-event or -disease activity) include Tau, P-Tau isoforms, TDP-43, and IL-6. The biological sample levels of this set of biomarkers >10 days to months post-event is particularly useful in monitoring the transitioning of an early injury or disease or repair event into a late neurological or neurodegenerative condition.

These late markers might also be highly responsive to therapeutic treatments for injury, disease, or repair that serve to prevent or modulate the manifestation or transition from the initial injury, disease or repair event into late neurological or neurodegenerative conditions.

Table 1 shows examples of each of three temporal biomarker categories to compose a combinatory biomarker panel

TABLE 1

Three temporal biomarker categories to select from for composing combinatory biomarker panels.

| Temporal biomarker categories | Early | Intermediate | Late |
|---|---|---|---|
| Approximate temporal biomarker range from reference point (post injury, disease, or repair event): | ≤48 hours | >48 hours to ≤10 days | >10 day to months |
| Biomarkers for inventive combinatory temporal biomarker panel | GFAP, UCH-L1, VILP-1, NSE, S100B, GAD1, GAD2 | α-INT, NF-H, NF-M, NF-L, synapsins (synapsin-1/-2/-3), MBP, MOG, MAG, PLP, SV2A, SIRPα, TREM2, and complement proteins (C3, C4, C5, and Clq, C5b-9, CD68, CR3, C3b, iC3b), CD11b, TREM2, SIRPα, Nogo-66 receptor, DEC205, CX3CR1, CD68, CD45, CD47 | Tau, P-Tau, TDP-43 and IL-6 |

Table 1 shows how one can select at least one biomarker from each of the three temporal biomarker categories: early (Examples: GFAP, VILP-1, UCHL-1, NSE, S100B), intermediate (Examples: α-INT, NF-L, Synapsin-2, MBP, MOG) and, late (Examples: Tau, P-Tau, TDP-43 and IL-6) to achieve thus achieving a sustained and detectable overall injury, disease, or repair signals in blood over the early, intermediate, and late phases post-event (albeit pre-injury, -disease and -repair measurements from the reference point of the event, pre-events, are also described herein).

Example 4

In order to trace and monitor the natural temporal history and progress of CNS and PNS injury, disease, and repair from the early, intermediate, and late phases and have such as diagnostic, prognostic and monitoring clinical and therapeutic effect tracking (theranostic) utilities, a panel of temporal biomarkers is composed of at least one marker from the early phase subset, at least one marker form the intermediate subset and one marker form the late phase subset.

In one inventive embodiment, VISP-1-in early phase, synapsin in the intermediate phase and P-Tau in the late phase. In another inventive embodiment: (GFAP in early phase, «α-INT or MBP in the intermediate phase and IL-6, TREM,2 or complement C3 in the late phase.

Through combination-based detection method in the form of a neuroinjury temporal biomarker panel uniquely allows one to continuously track the distinct phases of injury, disease, or repair per FIG. 1.

Example 5

An alternative inventive embodiment relies on combination detection method is related to enhancing Tau isoform and P-Tau isoform detection. Tau and in particular, P-Tau are known to be elevated especially in the late phase post injury, disease, or repair. However, their levels are known to be very low (low picogram/milliliter (pg/mL) to subpicogram/mL levels).

One of the reason Tau and P-Tau might be detected in low levels is due to the various compartmentation of Tau/P-Tau in a biofluid such as blood to afford a ratio. For example, Tau can be present in free form in biofluids, or embedded or encapsulated in exosomes of or microvesicles (MV) derived from various injury-, disease-, or repair-linked cell types such as neurons, astroglia, oligodendrocytes or microglia/macrophage.

Example 6

Another reason elevated biofluid P-Tau is detected only at low levels even after injury disease, or repair with a given P-Tau epitope-specific assay (such as sandwich ELISA with a total Tau antibody or aptamer and a single P-Tau epitope-specific antibody or aptamer) is a result of Tau being pathologically phosphorylated at up to 70 different phosphorylation sites. Some of the sites detectable are phosphorylation sites at Ser-181, Ser202, Ser-205, Thr-231, Ser-396, Ser-404, and Ser-409.

The use of P-Tau herein is premised on the discovery that the Tau molecule in a pathologic state, such as injury, disease, or repair, is phosphorylated at some, but not all the potentially sites. This follows that all Tau molecules in a sample pool (such as a blood sample) might be only phosphorylated at one phosphorylation site (e.g., Ser202 at 20%). Similarly, low phosphorylation (e.g., 10-30%) at other sites such as Ser-181, Ser202, Ser-205, Thr-231, Ser-396, and Ser-404 are also likely. Upon addressing the nature of pathological phosphorylation of P-Tau, it becomes a suitable temporal biomarker in the present invention.

Example 7

To improve on the ability to detect P-Tau in a biological sample, a detection method is now provided: assuming each of these pathological phosphorylation site (Thr-181, Ser-202, Thr-231, Ser-396/Ser-404, Ser-409)—are also phosphorylated in about 20% of the all Tau molecules in a sample pool (such as a blood sample), a combination-based sandwich detection approach is used with a series of capture and detection antibody or aptamer pair that is composed of a total Tau antibody or aptamer combined with Thr-181, Ser-202, Thr-231, Ser-396/Ser-404 and Ser-409-specific antibodies within the same detection unit, to enable the simultaneous and combined detection of more molecules of Tau that are phosphorylated at multiple phosphorylation sites thereby enhancing of detection signals for P-Tau in a given biofluid sample by a factor of about 5 fold (when up to 5 capture/detection pairs are used in the same detection unit).

Figure 3:
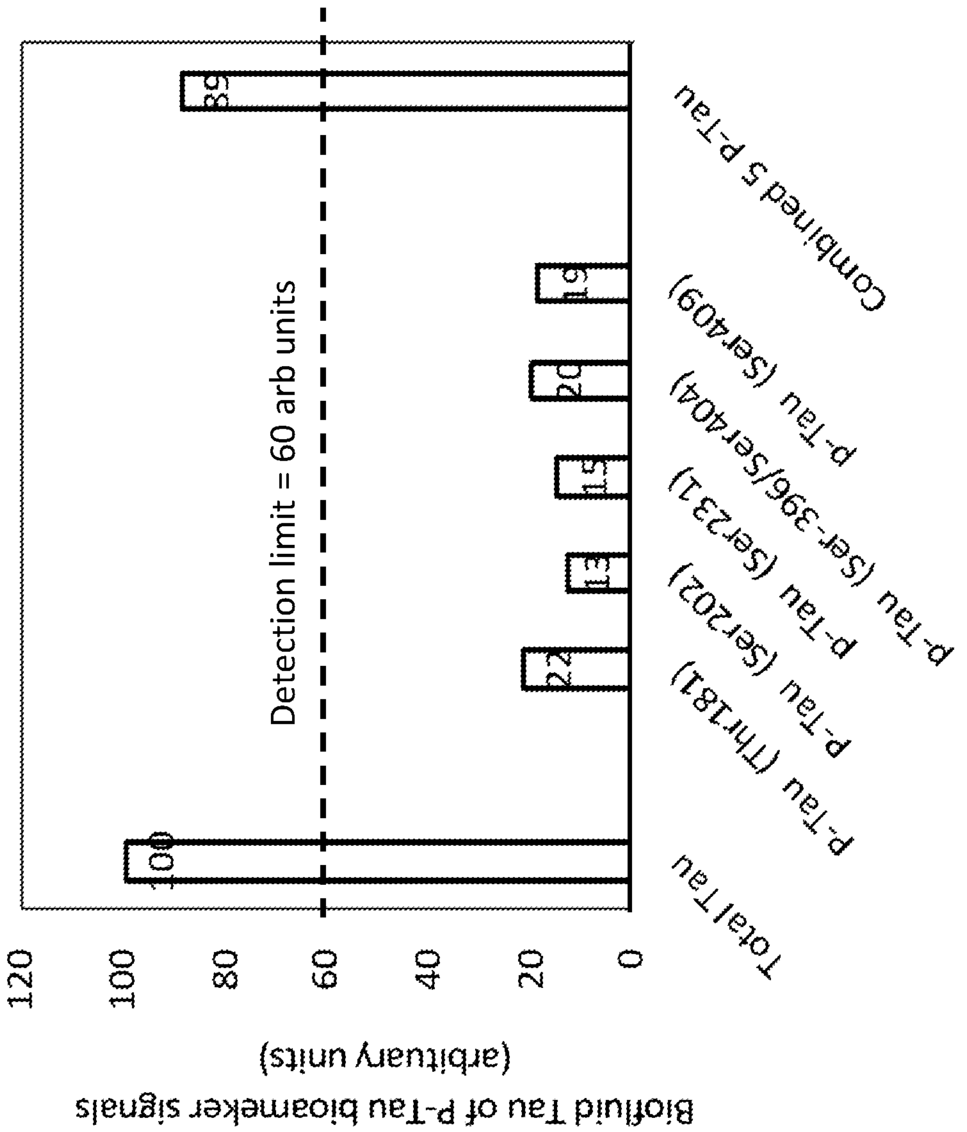
FIG. 3 is a plot of combining multiple phosphorylated Tau (P-Tau) signals by single or sandwich ELISA to enhance overall P-Tau signals for more robust detection and quantification in biofluid after CNS injury; with total Tau signals (100 arb units) (far left bar) being detectable using a sensitive detection platform (with quantification limit or threshold at 50 arb units (Dotted line); each of the single p-Tau levels, although present, are below robust limit of quantification (Bars in the middle); by combining all five P-Tau levels into one reading (far right bar)

FIG. 3 shows an example of combining multiple P-Tau signals by single or sandwich ELISA to enhanced overall P-Tau signals for more robust detection and quantification in biofluid after CNS injury. Total Tau signals (100 arb units) (far left bar) is detectable using a sensitive detection platform (with quantification limit or threshold at 60 arb units (dotted line). However,—each of the single p-Tau levels, although present, but are well below robust limit of quantification (Bars in the middle). However, by combining all five P-Tau levels into one reading (far right bar). Using this novel concept—the overall signals is about 5-fold of single P-Tau signals and thus is well above the detection threshold. This method makes P-Tau at detectable range similar that of total Tau.

Example 8

Tau phosphorylation sites are mainly at Serine and Threonine residues but also less frequently at Phospho-Ser (P-Ser), Phospho-Thr (P-Thr) and Phospho-Tyrosine (P-Tyr) specific antibodies with high affinity are known art and commercially available. A combination-based sandwich detection approach with a series of capture and detection antibody or aptamer pairs are composed of a total Tau antibody or aptamer combined with a P-Ser, P-Thr and/or P-Tyr-specific antibodies can enable the detection of more molecules of Tau that are phosphorylated at multiple phosphorylation sites in the same detection cell or unit. This combination-based detection enhances detection signals for P-Tau in a given biological sample by a factor of 3 to 5.

Table 2 shows that with sandwich ELISA format with total Tau capture/detection antibody (Ab) pair (MAb clone DA9, DA31), one can produce signals that are above assay platform qualification limit (e.g., at 60 units), but individual P-Tau southwestern-ELISA using total Tau Ab as capture and single P-Tau epitope as detection Ab (e.g. Ser-202 or clone CP13, or Thr231 or clone RZ3) yield signals below detection threshold. However, with the use of individual phospho-amino acid antibody as the detection antibody coupled with total Tau antibody as capture Ab, there is a 2 to 3-fold increase in detection signal strength. Furthermore, if P-Ser, P-Thr and/or P-Tyr MAb are combined as combinatory detection antibodies and coupled with total Tau antibody (e.g. DA9) as the capture Ab, a 3 to 5-fold increase detection signal strength is noted that is well above assay platform quantification limit. The use of P-Ser, P-Thr and P-Tyr antibody in combination with total Tau antibody is used to build a signal-enhanced P-Tau assay that is about detection/qualification limit.

TABLE 2

Use of P-Ser, P-Thr and P-Tyr antibody in combination with total Tau antibody to build signal-enhanced P-Tau assay that is above detection/qualification limit (e.g. at 60 units). For example, Combined Phospho-Ser Ab, Phospho-Thr and Anti- Phospho-Tyr Ab shows a relative signal of 124, that is well above the detection limit.

| Capture Antibody (Mab) or Aptamer (Ap) | Detection Ab or Ap | relative signals (Arb units) |
|---|---|---|
| Total Tau MAb (DA9) or Ap | Total Tau MAb (DA31) or Ap | 100 |
| Total Tau MAb (DA9) or Ap | P-Tau (Thr231) or Ap | 22 |
| Total Tau MAb (DA9) or Ap | P-Tau (Ser-202) Mab or Ap | 13 |
| Total Tau MAb (DA9) or Ap | Anti- Phospho-Ser Ab or Ap | 44 |
| Total Tau MAb (DA9) or Ap | Anti- Phospho-Thr Ab or Ap | 55 |

TABLE 2-continued

Use of P-Ser, P-Thr and P-Tyr antibody in combination with total Tau antibody to build signal-enhanced P-Tau assay that is above detection/qualification limit (e.g. at 60 units). For example, Combined Phospho-Ser Ab, Phospho-Thr and Anti- Phospho-Tyr Ab shows a relative signal of 124, that is well above the detection limit.

| Capture Antibody (Mab) or Aptamer (Ap) | Detection Ab or Ap | relative signals (Arb units) |
|---|---|---|
| Total Tau MAb (DA9) or Ap | Anti- Phospho-Tyr Ab or Ap | 25 |
| Total Tau MAb (DA9) or Ap | Combined Phospho-Ser Ab, Phospho-Thr and Anti- Phospho-Tyr Ab or Ap | 124 |

Example 9

Tau protein isoforms are known to contain many proline residues contiguous with downstream Ser or Thr residues. Importantly, such short epitopes (Pro-Ser, Pro-Thr) are targeted for a so-called proline-direction phosphorylation-carried out by Tau kinases such as Tau tubulin kinase isoforms, CDK5, casein kinase 2 and others. Pro-Ser and/or Pro-Thr specific antibodies is a known art in the field.

A combination-based sandwich detection is used with a series of capture and detection antibody or aptamer pairs that is composed of a total Tau antibody or aptamer combined with a Pro-Ser and/or Pro-Thr specific antibodies or aptamers to provide for the detection of more molecules of Tau that are phosphorylated at multiple proline-directed phosphorylation sites. For example, Table 3 demonstrates the use of proline-directed phosphorylated Ser and Thr epitope antibodies or aptamers in combination with total Tau antibody or aptamer can be used to build a signal-enhanced P-Tau assay that is above the assay detection/qualification limit (e.g., at 60 units). This combination-based detection of P-Tau with both Pro-pSer and Pro-pThr) fulfill the purpose of detection signal enhancement for P-Tau in a given biological sample by a factor of 5.

TABLE 3

The Use of Proline-directed phosphorylated Ser and Thr epitope antibodies or aptamers in combination with total Tau antibody or aptamer to build a signal-enhanced P-Tau assay that is above the assay detection/qualification limit (e.g., at 60 units).

| Capture Antibody (MAb) or Aptamer (Ap) | Detection Ab or Ap | relative signals (Arb units |
|---|---|---|
| Total Tau MAb (DA9) or Ap | Total Tau MAb (DA31) or Ap | 100 |
| Total Tau MAb (DA9) or Ap | P-Tau (Thr231) or Ap | 22 |
| Total Tau MAb (DA9) or Ap | P-Tau (Ser-202) MAb or Ap | 13 |
| Total Tau MAb (DA9) or Ap | Anti-Pro-phospho-Thr MAb or Ap | 49 |
| Total Tau MAb (DA9) or Ap | Anti-Pro-phospho-Ser MAb or Ap | 53 |
| Total Tau MAb (DA9) or Ap | Combined Pro-pSer, anti-Pro-pThr MAbs or Aps | 102 |

Example 10

Injured, diseased, and repairing brain cells can release exosomes (with CD61 cell surface marker), and microvesicles (MV). Tau protein becomes encapsulated or embedded in exosomes of MV and release into extracellular fluid or other body biofluid (e.g., lymphatic fluid, cerebrospinal fluid, blood). P-Tau is also trapped or encapsulated within these exosomes and/or MV.

Exosomes have CD61, Alex-1 surface receptor and Tag101; MVs have surface glutamate receptors (NMDAR, GluR, mGLuR, GABAR and synapsin-1/-2/-3) if the MV originated from glutamatergic neurons, Glu transporter if the MV originated from astroglia; MOG, PLP, MAG, MBP or CD47 id the MV originated from oligodendrocytes; CD11b, CD45, CD68, TREM2, SIRPα if the MV originated from microglia or macrophage, a combination-based sandwich detection is provided with a series of capture and detection antibody or aptamer pairs that is composed of the following two groups of antibody or aptamer:

(A) a single P-Tau antibody or aptamer-based detection (from Thr-181, Ser-202, Thr-231, Ser-396/Ser404, and Ser-409-specific antibodies or aptamers, combination-based use of multiple P-Tau-specific antibodies or aptamers (including Thr-181, Ser-202, Thr-231, Ser-396/Ser404 and Ser-409-specific antibodies); and (B) surface glutamate receptors (NMDAR, GluR, mGLuR, GABAR and synapsin-1/-2/-3) if the MV originated from glutamatergic neurons, Glu transporter if the MV originated from astroglia; MOG, PLP, MAG, MBP, or CD47 if the MV originated from oligodendrocytes; CD11b, CD45, CD68, TREM2, SIRPα if the MV originated from microglia or macrophage.

Figure 4:
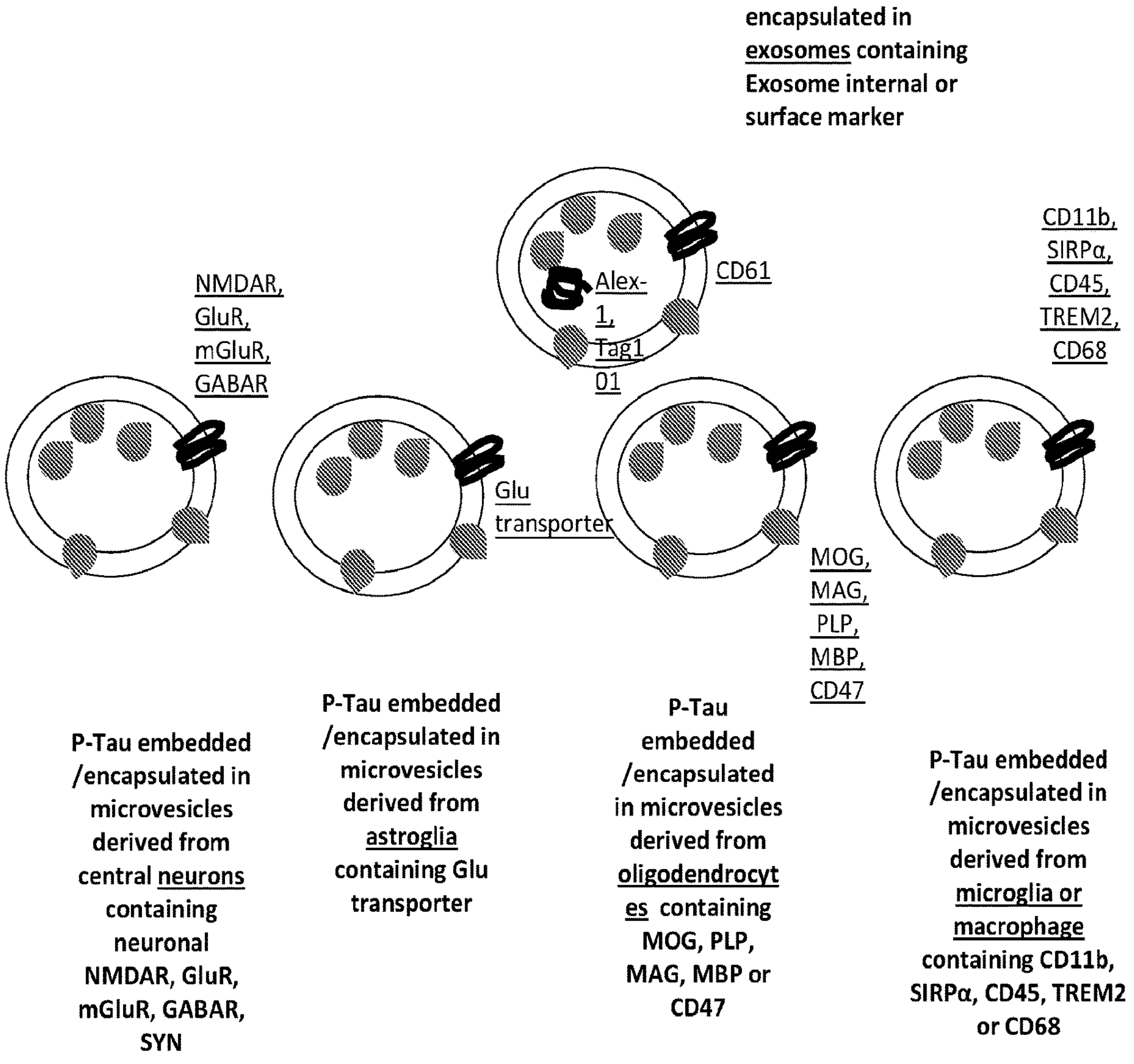
FIG. 4 is a schematic that shows a possible basis for Tau and P-Tau being present in microvesicles derived from neurons, astrocyte and potentially oligodendrocytes.

FIG. 4 shows that Tau and P-Tau is known to be present in not only neurons, but also astrocyte and potentially oligodendrocytes when cell debris or misfolded Tau or p-Tau protein is identified and phagocytosed (engulfed) by microglia or macrophages. This combination-based detection used alone or in combination with Tau and P-Tau antibodies or aptamers with exosomes and/or MV surface marker detection enhances signal detection for Tau and P-Tau in a given biological sample by a factor of 5.

An alternative detection method is to use biotinylated antibodies or aptamers specific to surface receptors of exosome, neuron, astrocyte, oligodendrocyte and/or microglia derived MVs (as shown in FIG. 3) by immunoprecipitation (e.g., with magnetic bead covalently linked to protein A/G that have affinity for IgG antibodies or aptamers or streptavidin for biotinylated antibody/aptamer binding). Then the pulled down and washed MV or exosomes are lysed with non-ionic detergents such as TritonX100 or NP40 (% v/v) and the content containing P-Tau species is then assayed and quantified by P-Tau direct (single antibody or aptamer) or sandwich ELISA (two antibodies or aptamers)

Example 11

A GFAP study (study design 1) was conducted on mice to determine the effects of controlled cortical impact (CCI).

The strain of mice used was C57BL/6 mice. The mice were injected with Mab (BD Pharmingen-Purified Mouse Anti-GFAP Cocktail (clones 1B4, 4A11, 2E1) Catalog No. 556330 with a concentration of 0.5 mg/ml. A first grouping of mice (N=12) Arm 1 were injected with saline, and a second grouping of mice (N=12) Arm 2 were injected with GFAP Mab. On day 1, immediately after CCI, immediate bolus dose via orbital vein (facial) at 20 ug/C57BL/6 mouse (approximately 25 g by weight) was injected in the mice. Subsequently, the same dose was repeated at day 3, 7, 14, 21, and 28.

In order to make endpoint assessments (study design 2) at day 3 and day 7, 200 μL serum samples were obtained. Terminal assessments of subjects were made on day 30 with 1 mL serum samples (serum mouse Tau (Quanterix)) obtained from each of the mice following a day 30 neurobehavioral assessment (EPM, Y-maze (see FIG. 6), MWM). Brain tissue samples from each of the mice were taken. Brain tissue lysate samples included cortex/hippocampus-ipsil, contra) (n=8). GFAP and GBDP levels were determined by quantitative immunblotting using a MSD Tau/P-Tau kit.

Figure 5C:
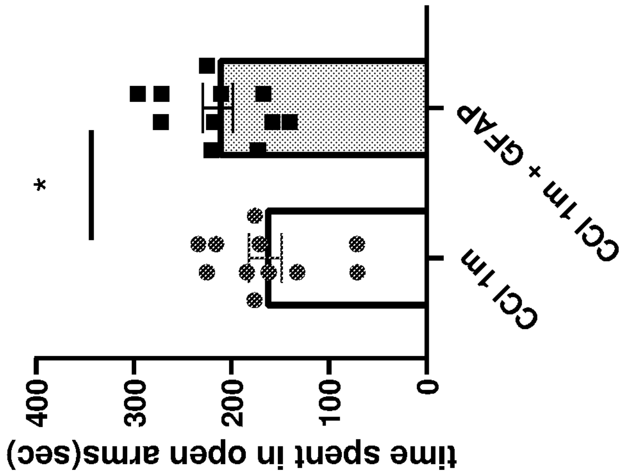
FIGS. 5A-5C are a series of graphs of the results for an elevated plus maze/EPM test for anxiety like behavior at thirty days from mice subjected to controlled cortical impact (CCI)—a form of TBI, without or with GFAP MAb therapy.
Figure 5B:
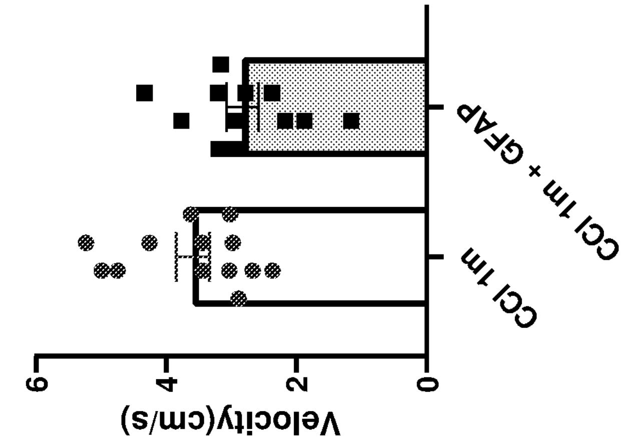
Figure 5A:
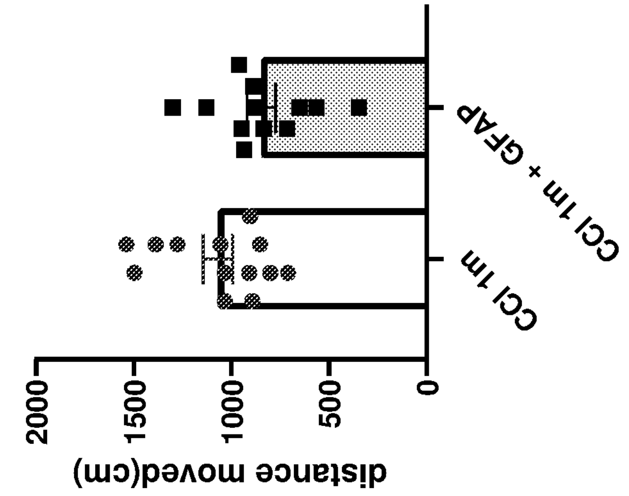

FIGS. 5A-5C are a series of graphs of the results for an elevated plus maze/EPM test for anxiety like behavior at thirty days from mice subjected to controlled cortical impact (CCI)—a form of TBI, without or with GFAP MAb therapy as described above. FIG. 5A shows the distance travelled by the mice in the treated groups. FIG. 5B summarizes the velocity of mouse movement for both the CCI group at one month and the CCI and GFAP Mab treated group. It is seen that velocity of movement are the same for both groups. FIG. 5C shows that the mice in the CCI+GFAP MAb group spent more time in the open arms of the maze-thus showing less anxiety behavior.

Figure 6A:
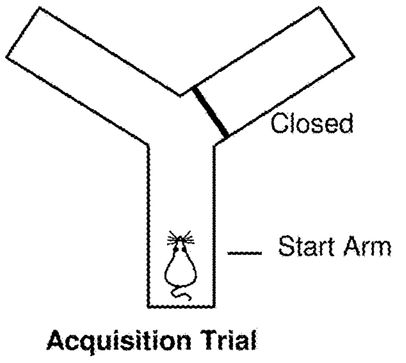
FIGS. 6A and 6B illustrate an acquisition trial Y-maze and a retrieval trial Y-maze used in cognitive function and memory test evaluation, respectively.
Figure 6B:
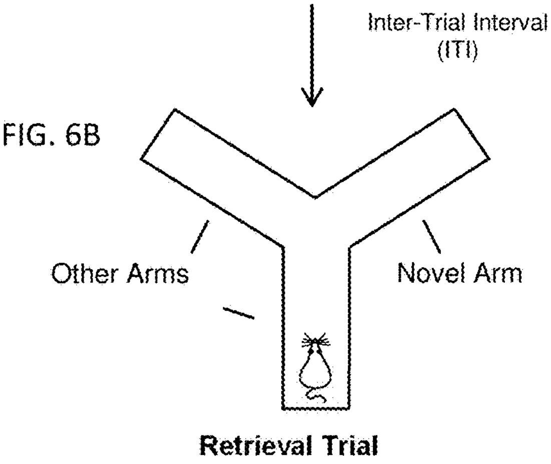
Figure 7:
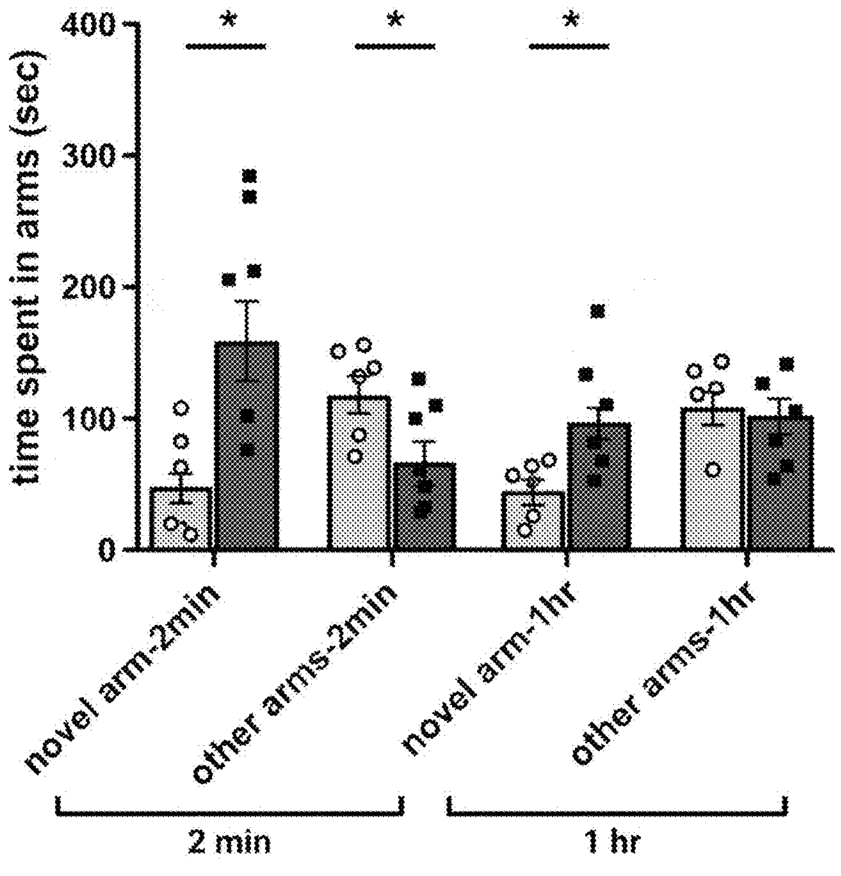
FIG. 7 is a graph showing time spent in arms of the retrieval Y-maze.

FIG. 6A illustrates acquisition trial Y-maze, and FIG. 6B illustrates the retrieval trial Y-maze used in the evaluation of cognitive function and memory test. At 30 days (1 month) from mice subjected to CCI, without or with GFAP MAb therapy. In FIG. 6A—Y-maze set-up: Mice were first trained in the acquisition trail with one arm closed. Then after 2 minutes and also after a 1 hour inter-trail interval (ITI), the mice are subjected to retrieval trial (twice) in FIG. 6B. As shown in FIG. 7, in the retrieval trials, at both 2 minutes ITI and at 1 hour ITI, CCI 1 month+GFAP Mab group spent more time than the CCI 1 month group in the novel arm. In addition, at 2 minutes ITI, GFAP group also spent less time in the other two arms (*$p<0.05$); n=7-8.

Example 12

Figure 8A:
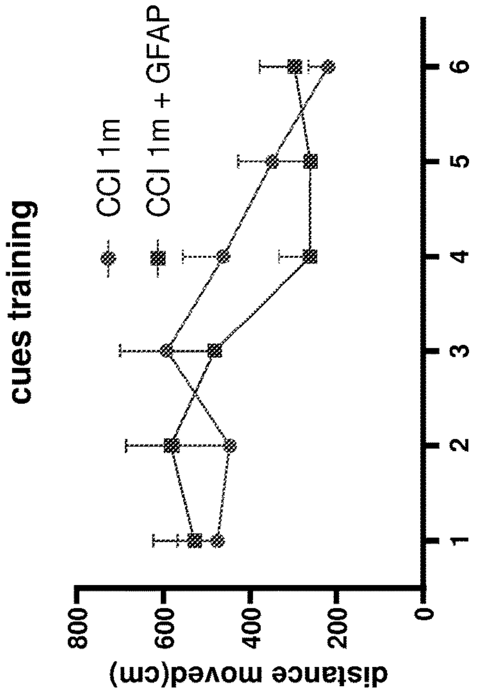
FIGS. 8A-8C illustrate the results for a Morris Water Maze (MWM) cognitive function and memory test.
Figure 8B:
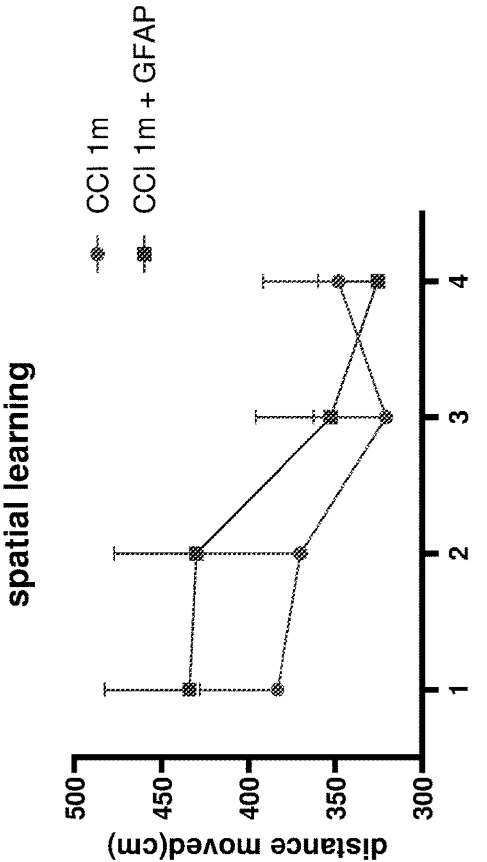
Figure 8C:
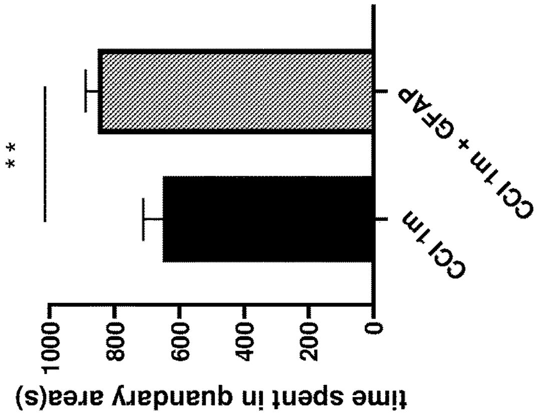

FIGS. 8A-8C illustrate the results for a Morris Water Maze (MWM) cognitive function and memory test. At 24-30 days (1 month) for mice subjected to CCI, without or with GFAP MAb therapy, were subjected to MWM cue training. FIG. 8A shows cues training. FIG. 8B shows spatial learning. FIG. 8C shows the mice subjected to probe trial. At the training/learning stage, both CCI 1 month and CCI 1 month+GFAP MAb groups have the same pattern in distance moved during both cues training stage and spatial learning stage. At probe trial stage, both CCI 1 month+GFAP Mab group spent more time than the CCI 1 month group in the target quadrant area (**$p<0.01$); n=12.

Example 13

Figure 9A:
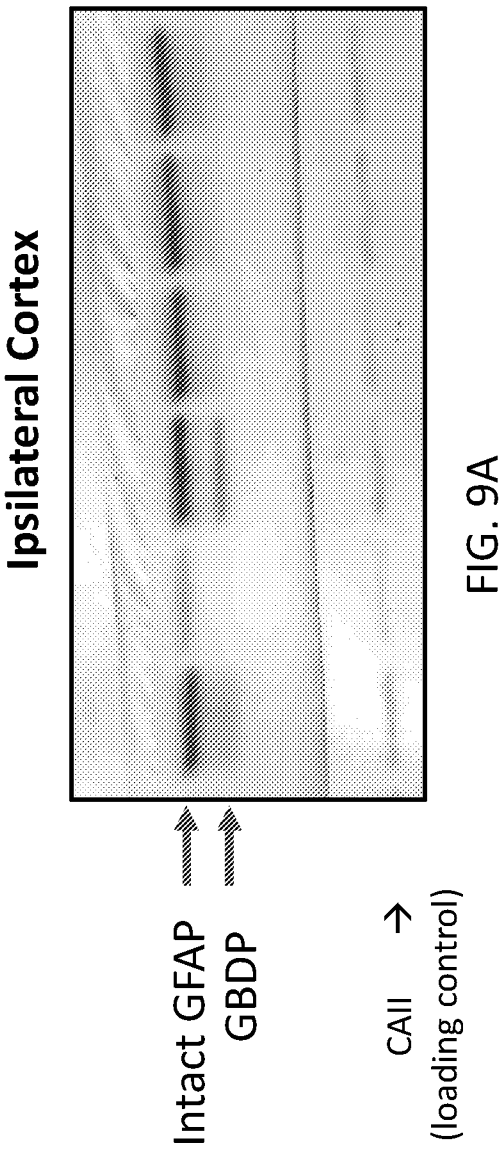
FIGS. 9A and 9B show immunblotting of the ipsilateral cortex (IC) and immunblotting of the ipsilateral hippocampus (IH), respectively that are probed with anti-GFAP antibodies to show the relative levels of GBDP (mainly 40 kDa) in addition to intact GFAP (50 kDa) (N=3)
Figure 9B:
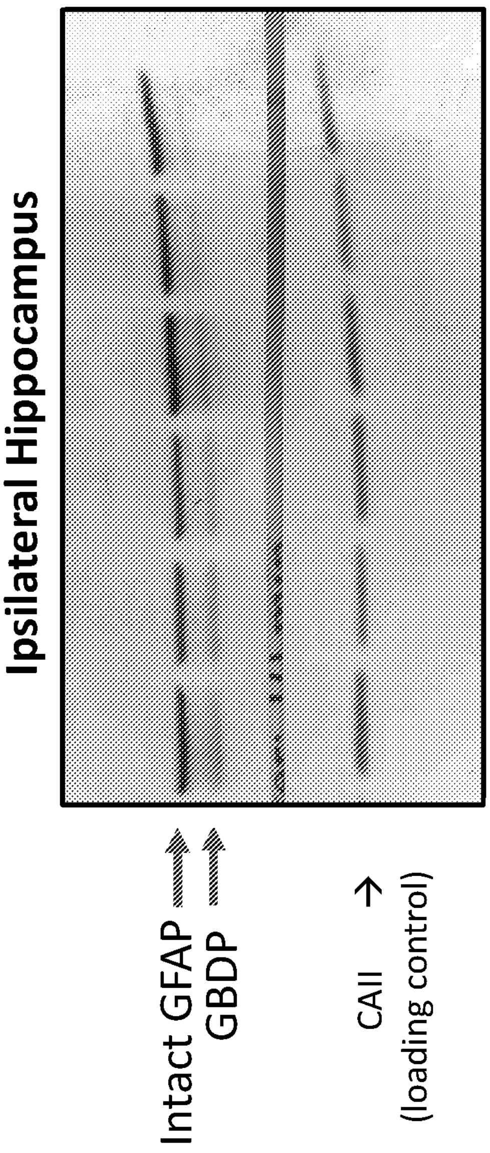
Figure 10:
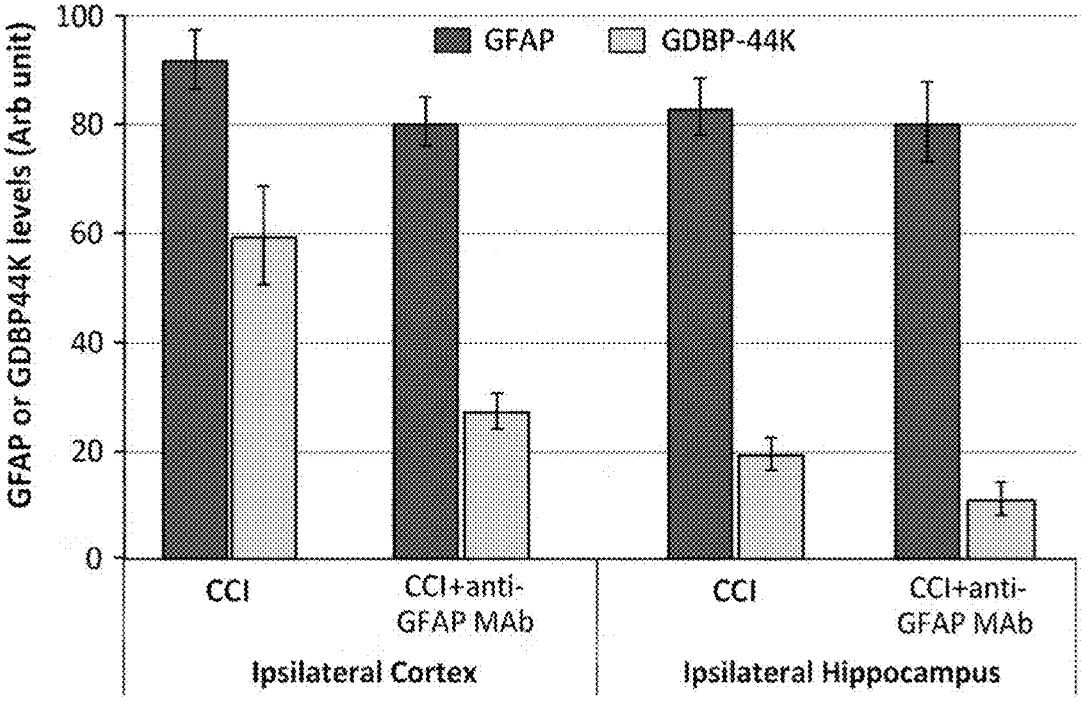
FIG. 10 is a graph showing densitometric quantification of both intact GFAP and GBDP bands (mean+SEM)

An experiment was conducted for post-injury immunization therapy with mouse anti-GFAP antibody suppressed GBDP levels. FIG. 9A shows immunblotting of the ipsilateral cortex (IC), and FIG. 9B shows immunblotting of the ipsilateral hippocampus (IH), that are both probed with anti-GFAP antibodies to show the relative levels of GBDP (mainly 40 kDa) in addition to intact GFAP (50 kDa) (N=3). FIG. 10 is a graph showing densitometric quantification of both intact GFAP and GBDP bands (mean±SEM). The intact GFAP levels are the same for both CCI and CCI+GFAP MAb groups. However, the levels of GBDP in both ipsilateral cortex and ipsilateral hippocampus were significantly attenuated in the CCI+GFAP MAb group. Not intending to be limited to a particular theory, it is conceptualized that GBDP is first produced by TBI (CCI) induced calpain protease activation in injured astrocytes, then GBDP is released into extracellular fluid and might have neurotoxic effects. This data shows that systemic GFAP Mab treatment in fact has the capacity to fulfil target engagement by reaching this extracellular pool of GBDP in the brain, and subsequently reducing its load presumably by IgG mediated phagocytosis/clearance by microglia and macrophage.

Example 14

Figure 11:
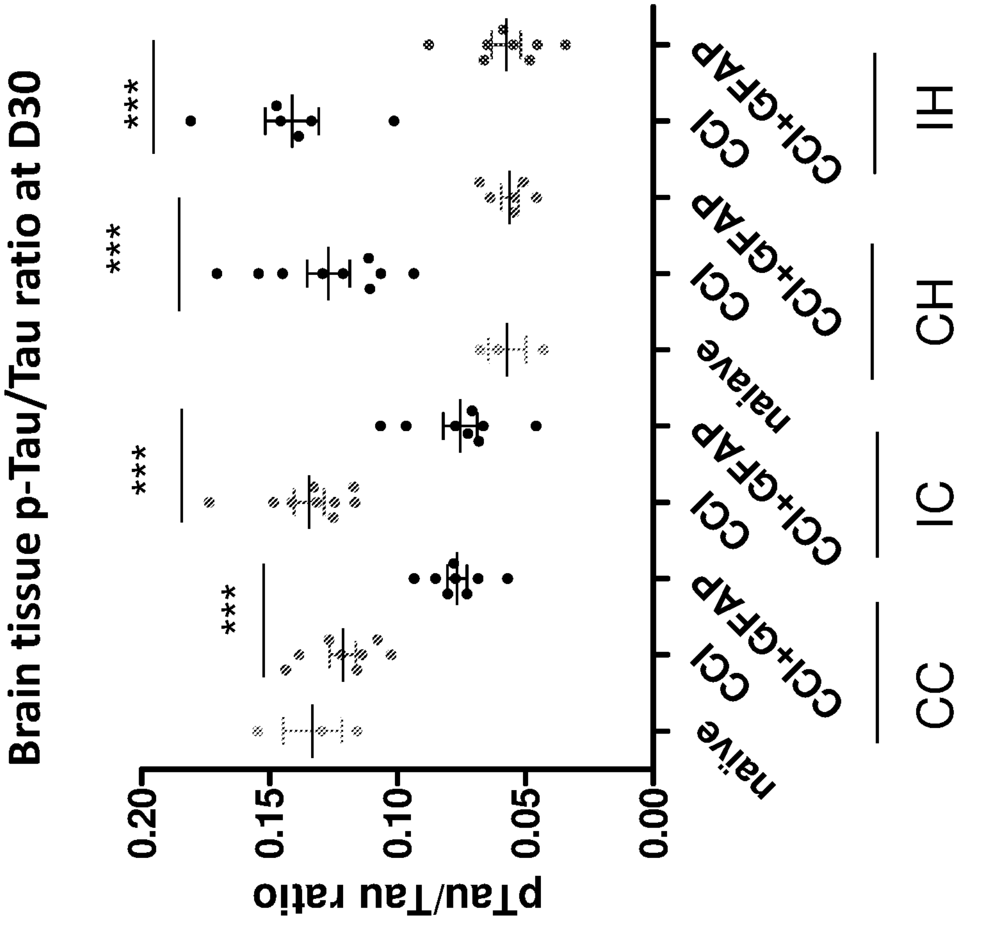
FIG. 11 is graph showing antibody attenuated P-Tau/Total Tau ratio in brain tissue for post-injury immunization therapy with mouse anti-GFAP MAb antibody.

An experiment was conducted for post-injury immunization therapy with mouse anti-GFAP MAb antibody in order to show attenuated P-Tau/Total Tau ratio in brain tissue with naïve n=4 (for comparison), CCI and CCI+GFAP MAb n=8 as shown in FIG. 11. At one month post-injury, brain tissue from different regions were used to prepare brain lysate that were equalized by protein assay to 1 mg/mL: ipsilateral cortex (IC) and ipsilateral hippocampus (IH), contralateral cortex (CC) and hippocampus cortex (CH), respectively. (*$p<0.05$, **$p<0.01$, *$p<0.001$) Both Total Tau and P-Tau (Thr-231) were assayed with the mesoscale discovery (MSD) duplex kit. In all tissue samples, the ratio of P-Tau/T-Tau was reduced about 2-fold. Since P-tau is associated with post-TBI neurodegeneration and tauopathy. These effects of GFAP MAb treatment are interpreted as neuroprotective and anti-neurodegeneration.

Example 15

Figure 12:
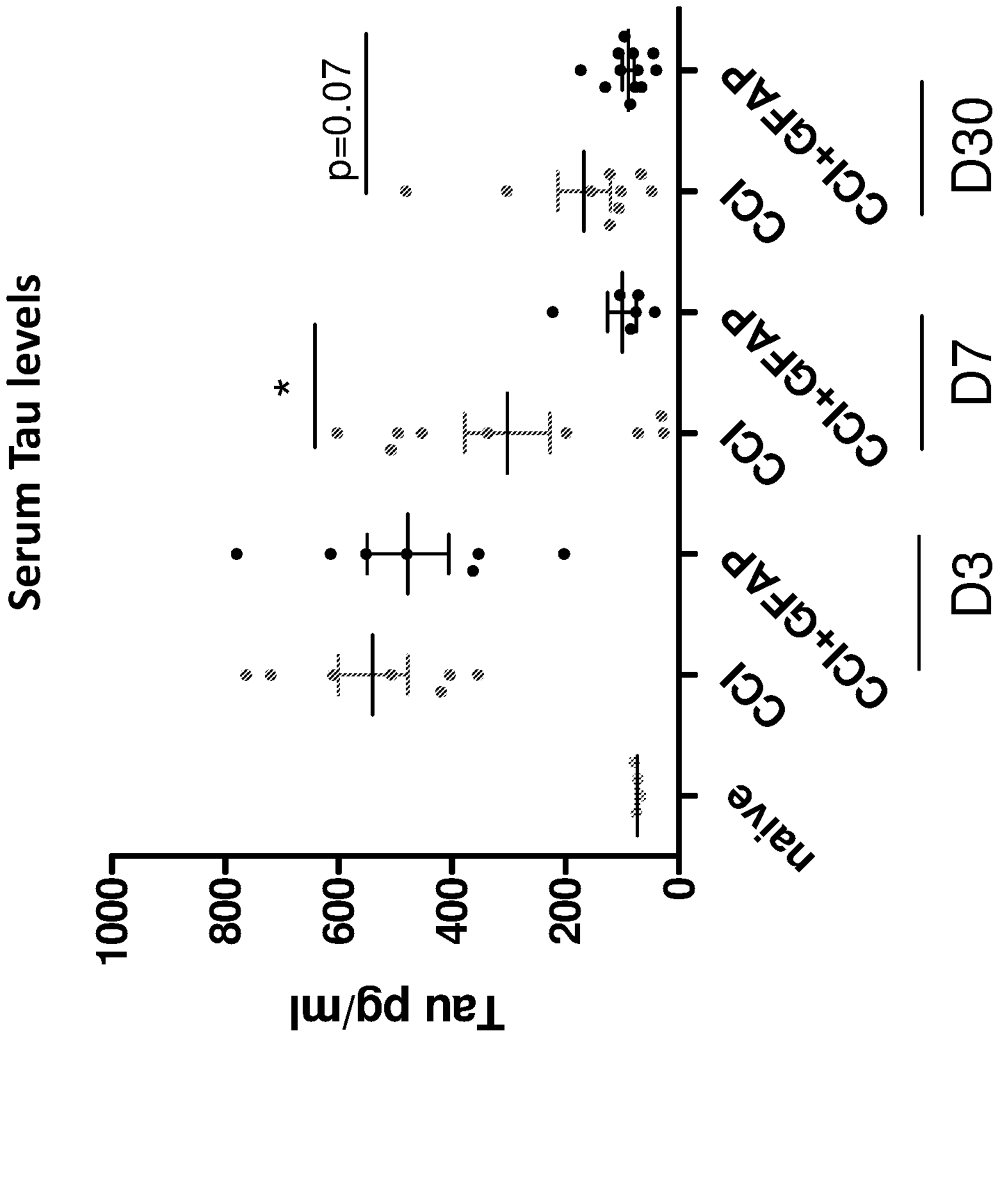
FIG. 12 is a graph showing serum tau levels in blood samples post-injury immunization therapy with anti-GFAP MAb at day 3, day 7, and day 30.

An experiment was conducted for post-injury immunization therapy with anti-GFAP MAb antibody reduced tau released into circulation (serum fraction) with naïve n=4 (for comparison), CCI and CCI+GFAP MAb n=7-10. As shown in FIG. 12, at day 3 (D3), day 7 (D7) and day 30 (D30-1 month) post-injury, blood samples were collected and processed to serum fraction. Tau was measured using a high sensitivity Quanterix mouse tau kit (it is noted that P-Tau mouse tau kit was not available for use at the time of this study-thus P-Tau in serum samples was not measured). There were strong elevations of tau at all three time points compared to naïve, especially in day 3 and day 7. By day 7 of GFAP MAb treatment, the levels of released tau was significantly attenuated (*$p<0.05$). Since tau release into blood has been shown to be associated with post-TBI neurodegeneration and tauopathy, these effects of GFAP MAb treatment are interpreted as neuroprotective and anti-neurodegeneration.

Example 16

Figures 1, 13A:
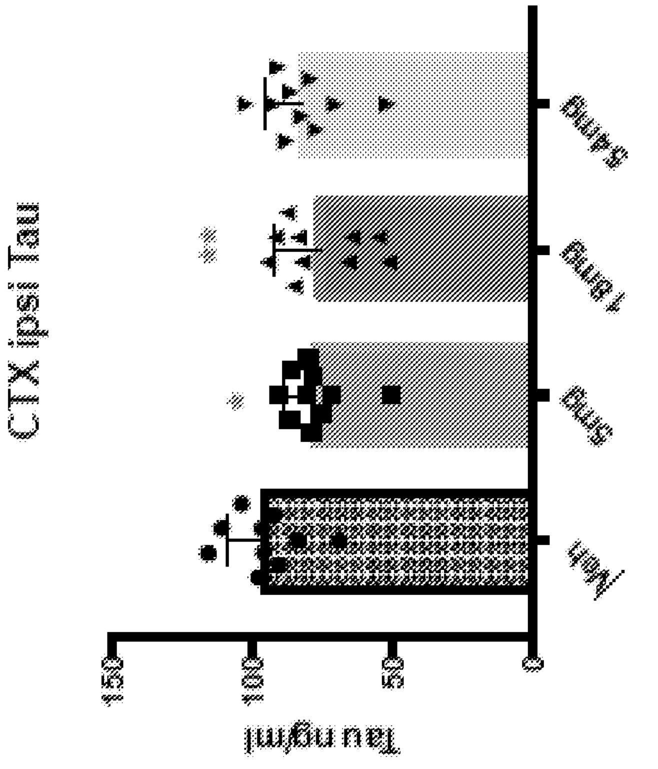
Figures 2, 13A:
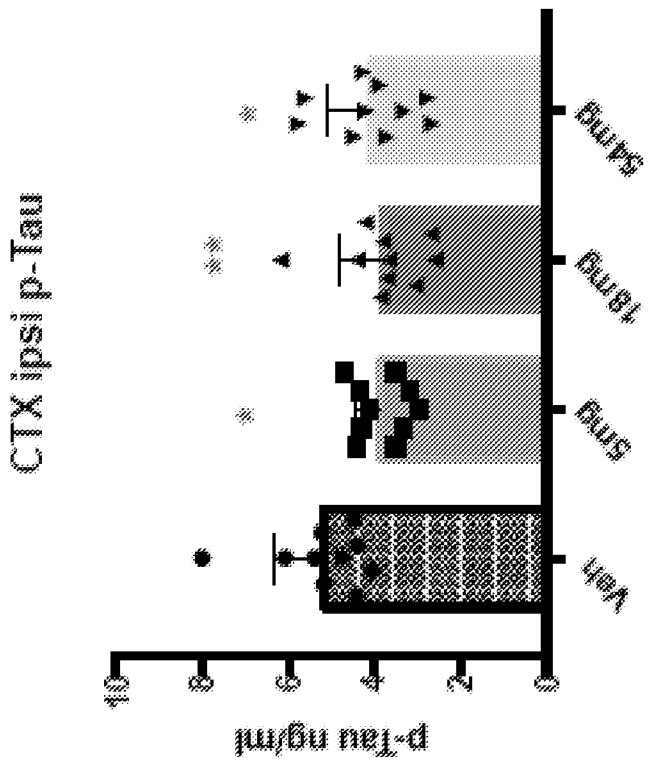
Figures 2, 13B:
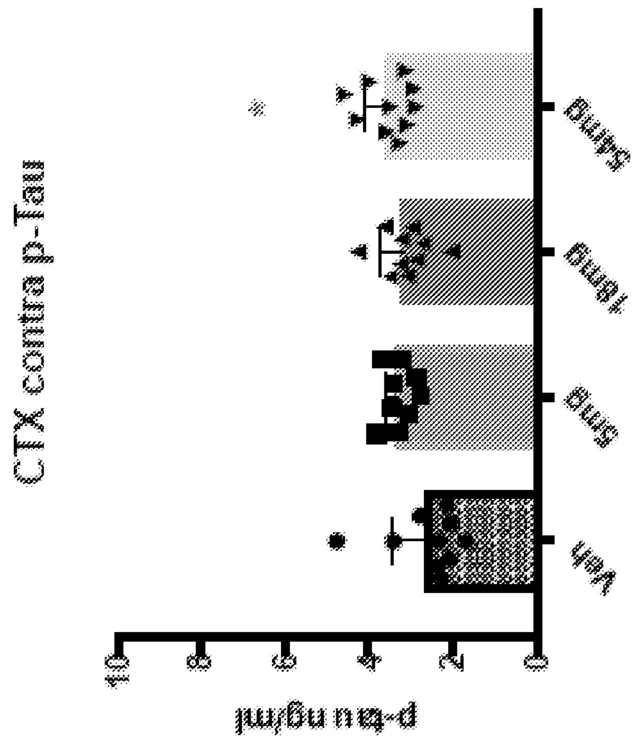
Figures 1, 13B:
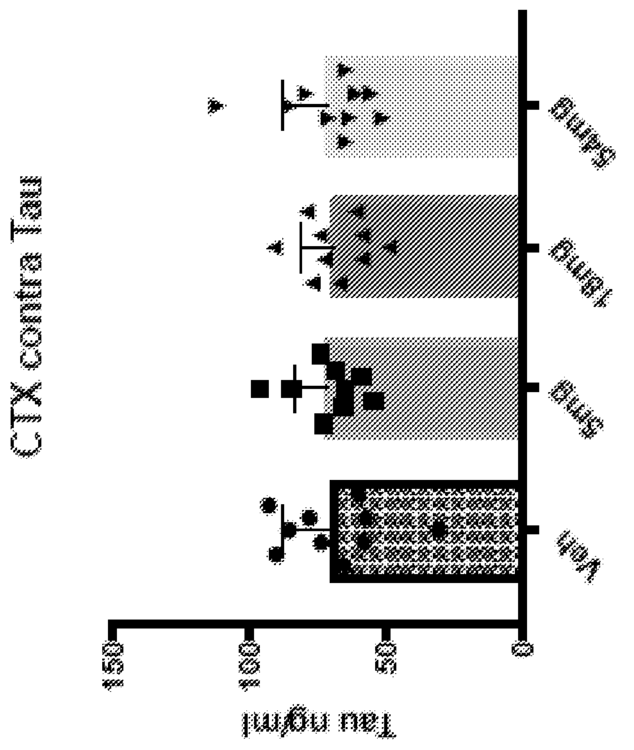
Figures 1, 13C:
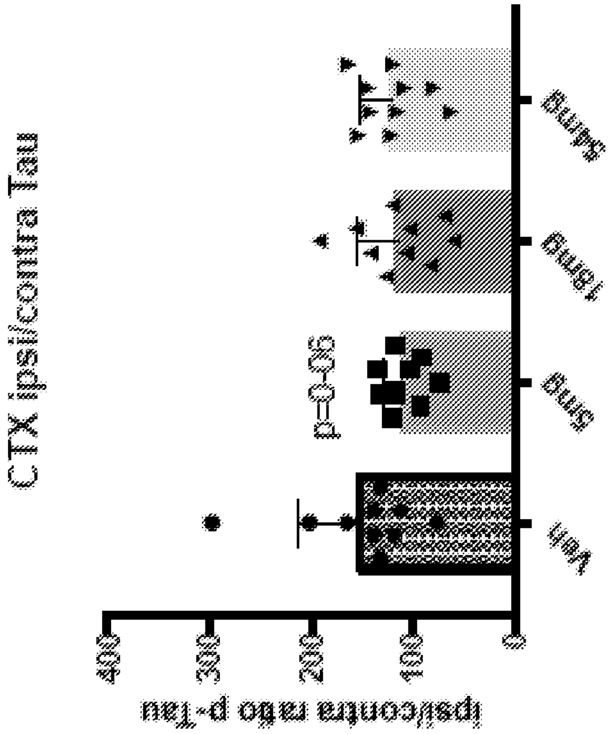
Figures 2, 13C:
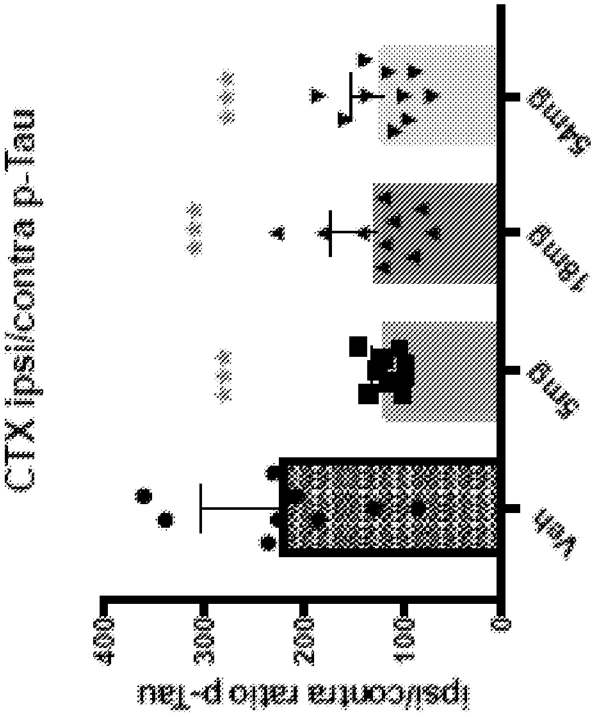

An experiment was conducted to provide evidence of the efficacy of temporal pharmacodynamic (PD) biomarker-powered precision medicines for targeting SV2A. Saline vehicle (veh) or levetiracetam (LEV) was administered at 5, 18 and 54 mg/kg in a controlled cortical impact (CCI) model in CD1 mice (male, 8 weeks old, n=10 per group) and measured PD biomarkers in the ipsilatleral (ipsi) and contraleteral (contra) cortex (ctx) and hippocampus (hippo) at 1 day post injury. A striking reduction was observed in temporal PD biomarkers for LEV-treated CCI subjects (vs. veh), as illustrated in FIG. 13C-2 where ipsilateral/contralateral p-Tau levels showed statistically significant differences between LEV-treated subjects vs. vehicle-treated subjects. (***=$p<0.001$). Thus, there is unexpected evidence of the effectiveness of temporal pharmacodynamic (PD) biomarker-powered precision medicines for targeting GFAP and GFAP breakdown products (GBDPs), Tau, P-Tau, GFAP, etc.

Example 17

Figure 14B:
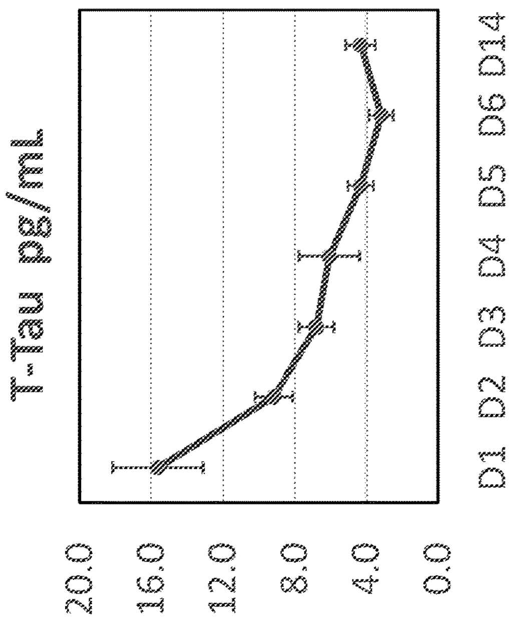
FIG. 14A-14C are a series of graphs that show that with the use of severe TBI serial serum samples, there are different temporal profiles for blood levels of P-Tau (Thr-231) (in pg/mL), T-Tau (in pg/mL) (measured with Quanterix SIMOA assay kits) and the calculated P-Tau/T-tau ratio in severe TBI subjects, respectively.
Figure 14A:
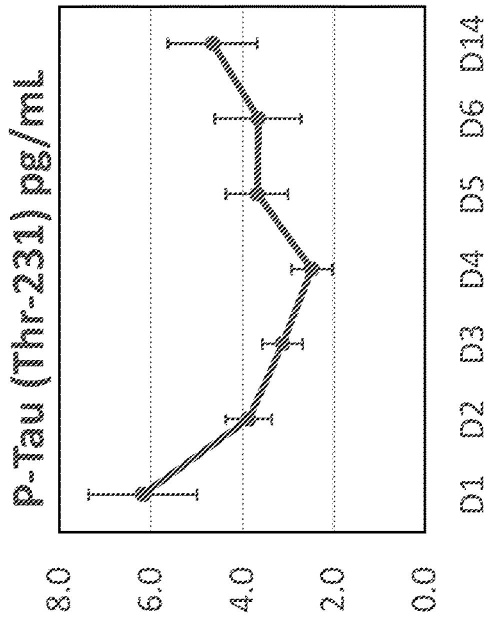
Figure 14C:
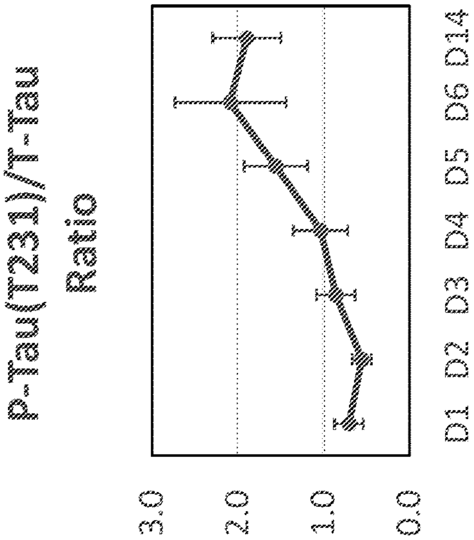

FIGS. 14A-14C show that with the use of severe TBI serial serum samples, there are different temporal profiles for blood levels of P-Tau (Thr-231) (in pg/mL), T-Tau (in pg/mL) (measured with Quanterix SIMOA assay kits), and the calculated P-Tau/T-tau ratio in severe TBI subjects. As observed in FIG. 14B, T-tau has peak level at day 1 followed by the decline pattern. However as seen in FIG. 14A, P-Tau on the other hand as an acute peak, but then takes on a U-shape curve and has a second peak at day 14. Lastly, as shown in FIG. 14C, the same sample P-Tau/Total Tau ratio has yet a third temporal pattern that continues to rise over time to at least Day 6 and Day 14. This data supports the observation that different Tau, P-Tau, and measurement of P-Tau/Tau ratio take on different temporal biomarker profiles and are useful as therapeutic treatment monitoring tools. The temporal biomarker profiles provide different response profile as a results of therapeutic treatment of TBI. In addition, concurrently measuring Tau, and P-Tau, and measurement of P-Tau/Tau ratio over a period of days after initiation of therapeutic treatment post-injury might provide the uniquely useful therapeutic response and/or pharmacodynamic response information during the course of clinical TBI drug trial or TBI patient treatment.

Example 18

Figure 15B:
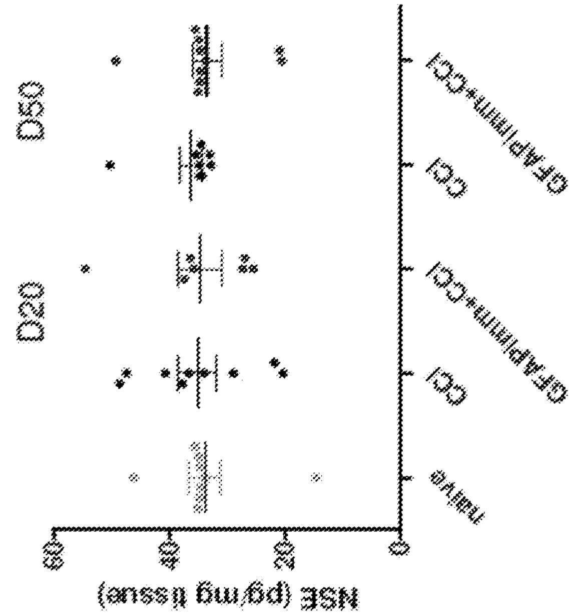
FIGS. 15A-15C show the effect of pre-injury GFAP immunization on NSE levels in CCI mice in ipsilateral cortex (FIG. 15A), ipsilateral hippocampus (FIG. 15B), and serum (FIG. 15C) as indicated.
Figure 15A:
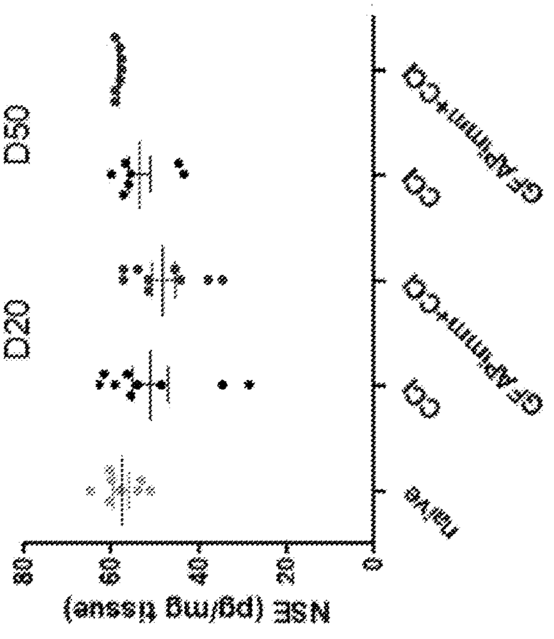
Figure 15C:
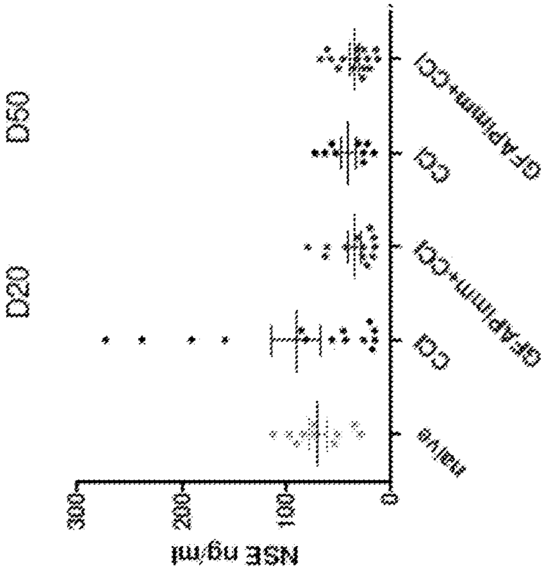
Figures 1, 16A:
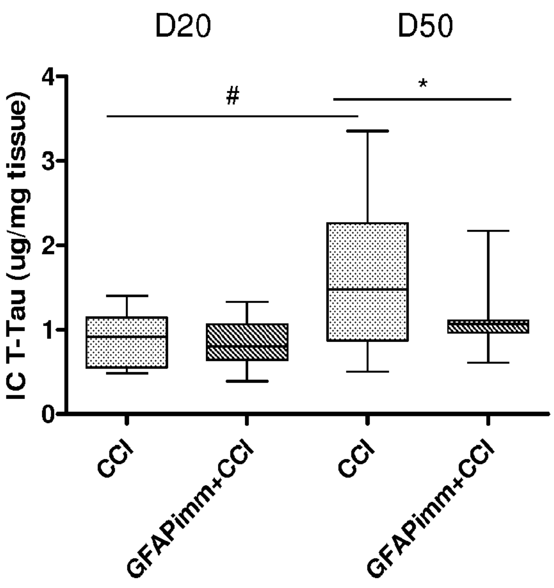
Figures 1, 16B:
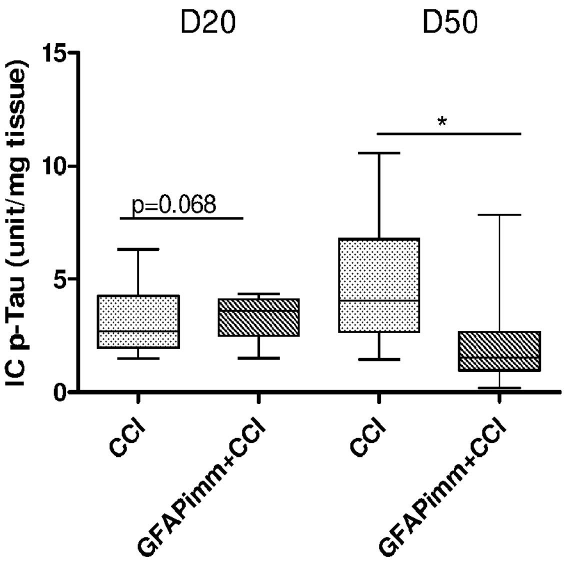
Figures 2, 16A:
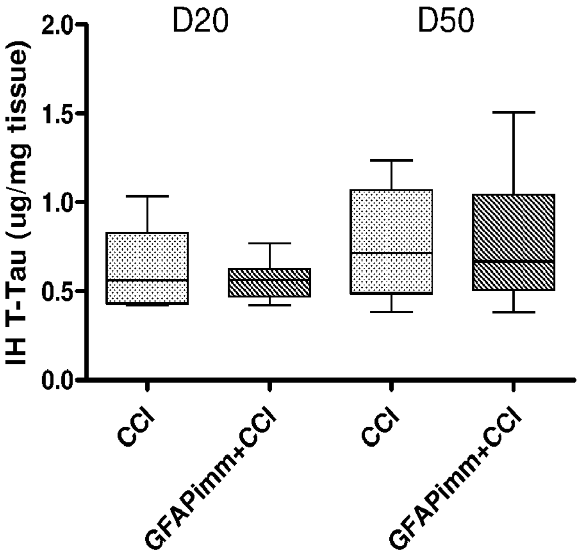
Figures 2, 16B:
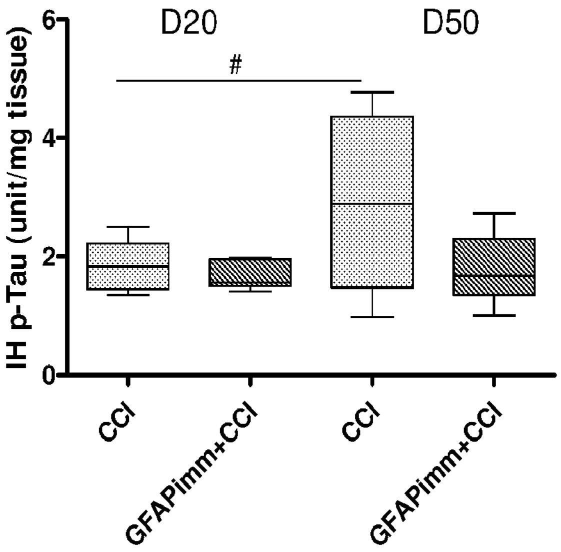
Figures 1, 16C:
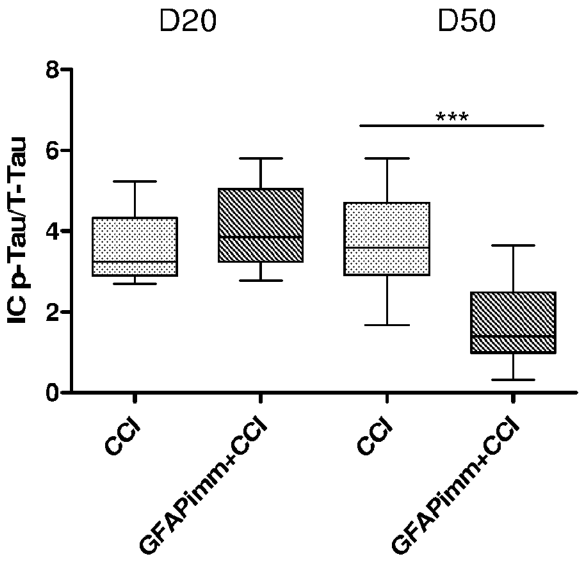
Figures 2, 16C:
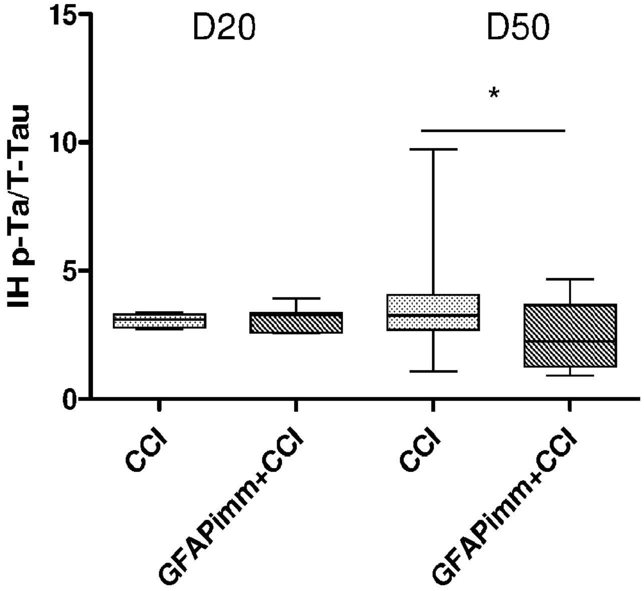

As GFAP, pNF-H, NSE, Tau, and P-Tau indicate the molecular and biochemical changes induced by TBI, the levels of these proteins were measured in serum as well as brain tissues (cortex and hippocampus) at a chronic phase (Day 20 and Day 50 post-TBI). Evidence showed that biofluid (CSF, blood) levels of most acute TBI markers will return to baseline levels within a matter of days following TBI, especially for those who suffered from mild brain injury. However, subacute and chronic effects of TBI can persist for months following the initial injury event. NSE is an acute marker which can reach a peak level within few hours. Thus, there would be no detectable change at either Day 20 or Day 50 following TBI as shown in FIGS. 15A-15C.

Example 19

Tau plays a pivotal role in the pathogenesis of neurodegenerative disorders. Hyperphosphorylated Tau (P-Tau) aggregates of tau, forming neurofibrillary tangles (NFTs), constitute a pathological hallmark of Alzheimer disease (AD) and fronto-temporal dementia (FTD) and PD. Tau suppression in a neurodegenerative mouse model improves memory function and stabilized neuron numbers. Tau, P-Tau or P-Tau/T-Tau ratio also are considered chronic TBI biomarkers relating to neurodegeneration. As shown in FIGS. 16A-1-16C-2, chronic tauopathy after TBI is seen, with a higher total-tau or P-tau expression in either cortex (IC) or hippocampus tissues (HC) at Day 50 compared to that at Day 20 was found. GFAP immunization reduced the PTau/T-Tau ratio in injured cortex and injured hippocampus at Day 50 post-injury. Serum Tau and P-Tau were not examined since currently there still are limitations to robust detection of Tau and P-Tau levels in rodent serum. Also, the P-Tau concentration is about 2-5% of total Tau (data not shown). Thus, more sensitive methods are required for P-Tau assay in rodent serum samples. Overall, GFAP pre-immunization showed beneficial effects after TBI, demonstrated by several TBI biomarkers, which indicates a clinical use for the treatment. Importantly, the ability of GFAP immunization to attenuate tauopathy (increased Tau and P-Tau levels in brain and biofluids) demonstrates that such immunization treatment can attenuate neurodegenerative conditions with a tauopathy component, such as CTE, AD, PD and FTD.

Example 20

A test was conducted to determine the effect of GFAP immunization to alleviate post-injury anxiety and improves cognitive functions.

Figure 17A:
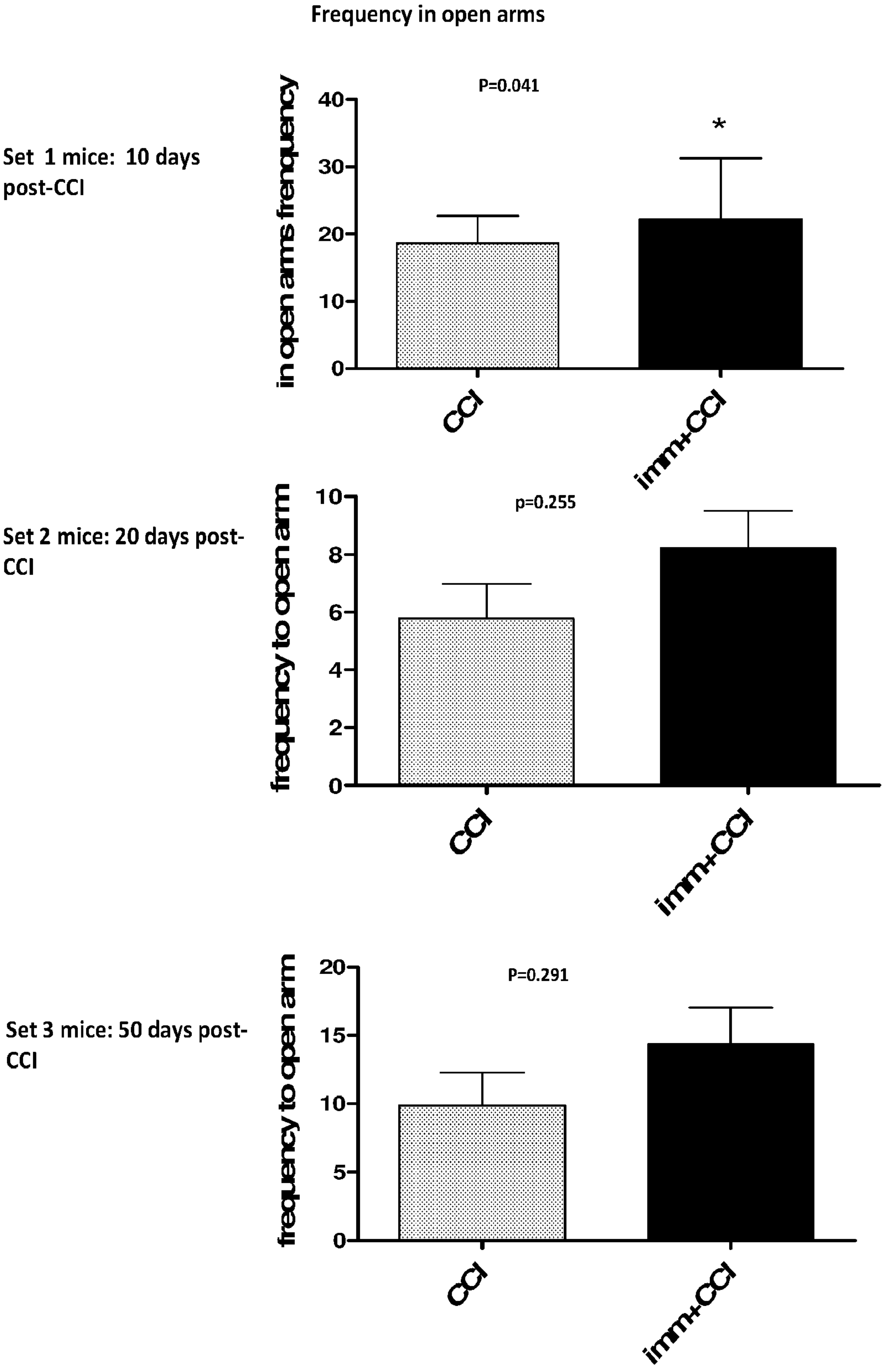
FIGS. 17A-17B illustrate post-TBI anxiety-like behavior that was examined using the elevated plus maze (EMP) test, where
Figure 17B:
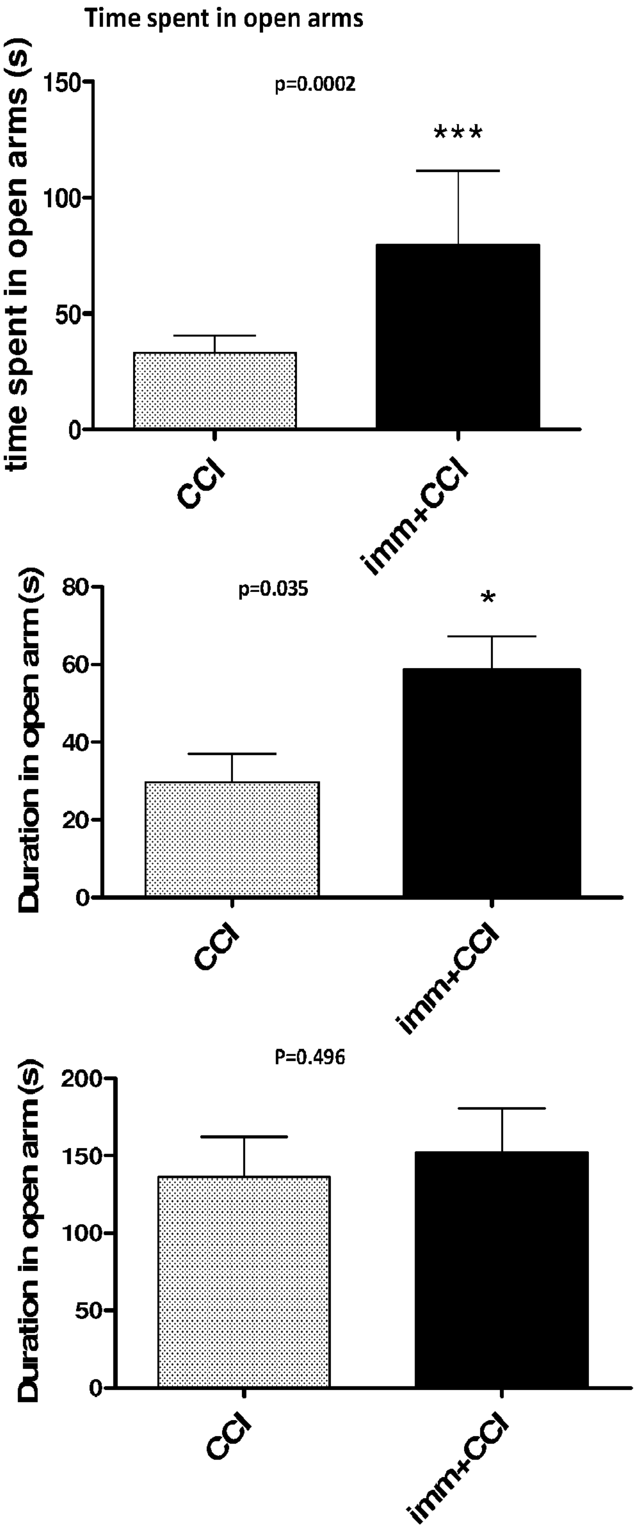

Post-TBI anxiety-like behavior was examined using the elevated plus maze (EMP) test, which is followed by the cognitive and memory (Morris water maze (MWM)) test on three individual sets of mice. Each mouse only experienced one behavioral test. Three time courses after injury were used: 10 days, 20 days and 50 days post-CCI surgeries. FIG. 17A shows the frequency in open arms; FIG. 17B shows the time spent in open arms. In the EMP test, at 10 days post-CCI, the GFAP pre-immunization group had a significantly higher frequency of entering the open arms and spent more time in the open arms, indicating this group mice presented less anxious behavior. At 20 days, mice undergoing GFAP immunization still had more duration in the open arms. However this benefit did not last to 50 days.

Following the EMP tests, 5 days of MWM tests were performed to test the behavioral function in mice, evaluated at 10, 20, and 50 days post CCI. The CCI model was relatively modest in terms of inducing a deficit in latency to find the hidden platform in the MWM test. FIG. 18A shows the time spent in the correct quadrant area, indicating the memory function, and FIG. 18B shows the spatial learning curve, related to the spatial leaning function. At 10 days, mice which underwent GFAP immunization showed a trend of increased memory function ($p=0.085$) by spending more time in the quadrant area. The only significant effect of GFAP immunization on MWM test outcomes was an improvement in memory function at 20 days post injury. However, there was no such effect at 50 days (see FIG. 18A). No effects were observed on spatial learning at these three time points (see FIG. 18B). Thus, pre-immunization with GFAP protein improved cognitive deficits, but did not improve spatial learning. In FIGS. 18A and 18B, * indicates $p<0.05$ compared to the CCI group.

Example 21

A test was conducted to determine the effect of GFAP antibody treatment in mice on post-traumatic brain injury.

Mouse strain: C57BL/6 mice was used. For Post-traumatic brain injury antibody treatment in mice Mouse MAb (BD Pharmingen—Purified Mouse monoclonal Anti-GFAP antibody cocktail (clones 1B4, 4A11, 2E1) Catalog No. 556330; concentration 0.5 mg/ml) was used. The study had three arms. Arm 1-controlled cortical impact (CCI, as a form of experimental TBI+saline (N=12), Arm 2-CCI+GFAP MAb (N=12). On day 1, immediately after CCI, immediate bolus dose of Purified GFAP Mab (mouse monoclonal antibody) in 0.9% saline via orbital vein (facial) at 20 ug/C57BL/6 mouse (approx. 25 g by weight) was given, followed by same dose at day 3, 7, 14, 21 and 28.

As an alternative follow-up MAb administration, following the initial bolus dose of anti-GFAP Mab via the orbital vein, an ALZET osmotic pump is implanted subcutaneously following the implant protocol of the ALZET osmotic pump (cat #1004). Briefly, a mid-scapular incision is made with 1.0-1.5 cm longer than the pump length. Use a hemostat into the incision to create a pocket. a filled pump is placed into the pocket, and then the incision is closed with sutures. GFAP Mab used (20 ug) is diluted in total 100 μL with 0.9% saline and pumping rates is 0.11 μL/hr.

For assessment, Day 3, Day 7 (200 μL) Serum samples are obtained as well as terminal (Day 30) serum samples (1 mL) after neurobehavioral assessment (which include elevated plus maze/EPM for anxiety like behavior assessment and Y-Maze and Morris water maze (MWM)—both as cognitive/memory function assessments. Brain tissue are pulverized and lysed with Triton-X-100 (1%) lysis buffer containing 50 mM Tris-HCl, 5 mM EDTA, 1 mM dithiothreitol and protease and phosphatase inhibitor cocktail (EMD Bioscience). Brain tissue (ipsilateral, contralateral cortex or hippocampus are analyzed for brain biomarker protein levels using enzyme linked immunosorbent assay (ELISA) or denaturing-gel electrophoresis following with electrotransfer and immunblotting with antibody against neurobiomarkers- and enzyme (alkaline phosphatase)-substrate based colorimetric development.

Taken together, Examples 11-21 show that post-TBI immunotherapy treatment with anti-GFAP monoclonal antibody for about 28 days improve neurobehavioral functional recovery in mice. In addition, brain tissue and blood-based neuroinjury biomarkers are attenuated by anti-GFAP monoclonal antibody treatment.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention but is not meant to be a limitation upon the practice thereof. The following claims, including all equivalents thereof, are intended to define the scope of the invention.

The invention claimed is:

1. A method for using an in vitro diagnostic device for detecting a phase, type or amplitude (severity) of an injury, disease, or repair in a subject, the method comprising:
obtaining a first biological sample from a subject;
applying said first biological sample to said in vitro diagnostic device, said in vitro
diagnostic device comprising a sample chamber for holding a biological sample collected from the subject, an assay module in fluid communication with the sample chamber, and a user interface, wherein an assay in said assay module comprises:
an early agent for detecting one or more early biomarkers present in said first biological sample of repair from the subject and released into said first biological sample by the injury, disease, or repair and the early biomarkers having an early peak amount in said first biological sample within 48 hours of the injury, disease, or repair, the one or more early biomarkers is glial fibrillary acidic protein (GFAP), a breakdown product of GFAP, visinin-like protein-1 (VILP-1), neuron specific enolase (NSE), S100 calcium-binding protein B (S100B), glutamate decarboxylase 1 (GAD1), glutamate decarboxylase 2 (GAD2), or a combination of the aforementioned proteins;
an intermediate agent for detecting one or more intermediate biomarkers present in said first biological sample of repair from the subject and released into said first biological sample by the injury, disease, or repair and the intermediate biomarkers having an intermediate peak amount after the early biomarkers peak amount and from 48 hours to 10 days of the injury, disease, or repair; the one or more intermediate biomarkers is α-internexin (α-INT), neurofilament protein-heavy chain (NF-H), neurofilament protein-medium chain (NF-M), neurofilament protein-light chain (NF-L), synaptic damage marker synapsin isoforms (synapsin-1, synapsin-2, synapsin-3, synaptic vesicle glycoprotein 2A), myelin basic protein (MBP), myelin oligodendrocyte glycoprotein (MOG), myelin oligodendrocyte associated protein (MAG), proteolipid protein (PLP), and complement proteins (C3, C4, C5, and C1q, C5b-9, CD68, CR3, C3b, iC3b), CD11b, TREM2, SIRPα, Nogo-66 receptor, DEC205, CX3CR1, CD68, CD45, CD47 or combinations of the forementioned proteins;
a late agent for detecting one or more late biomarkers present in said first biological sample from the subject and released into said first biological sample by the injury, disease, or repair and the late biomarkers having a late peak amount after the intermediate biomarkers peak amount more than 10 days of the injury, disease, or repair; the one or more late biomarkers is Tau, P-tau isoforms, TDP-43, IL-6, or combinations of the aforementioned proteins.

2. The method of claim 1, wherein the injury, disease, or repair is one of: traumatic brain injury (TBI), stroke, spinal cord injury (SCI), brain hemorrhage, Parkinson disease, Alzheimer's disease, chronic traumatic encephalopathy (CTE), epilepsy, Huntington's disease (HD), amyotrophic lateral sclerosis (ALS), frontal temporal dementia, hypoxic ischemic encephalopathy (HIE), mild to moderate TBI, neural damage due to drug or alcohol addiction, prion-related disease, multiple sclerosis (MS), diabetic neuropathy, chemotherapy-induced neuropathy, neuropathic pain, vanishing white matter disease, or other neurological or neurodegenerative disease.

3. The method of claim 1 wherein said biological sample is one of: blood, blood plasma, serum, sweat, saliva, cerebrospinal fluid (CSF), breath, and urine.

4. The method of claim 1 wherein the one or more late biomarkers is Tau, P-Tau isoforms, or a combination of any of the Tau or the P-Tau isoforms.

5. A method for using an in vitro diagnostic device for detecting a phase, type
or amplitude (severity) of an injury, disease, or repair in a subject, the method comprising:
obtaining a biological sample from a subject;
applying said biological sample to said in vitro diagnostic device, said in vitro diagnostic device comprising a sample chamber for holding a biological sample collected from the subject, an assay module in fluid communication with the sample chamber, and a user interface, wherein an assay in said assay module comprises:

an early agent for detecting one or more early biomarkers present in said first biological sample from the subject and released into said first biological sample by the injury, disease, or repair and the early biomarkers having an early peak amount in said first biological sample within 48 hours of the injury, disease, or repair; the one or more early biomarkers is glial fibrillary acidic protein (GFAP), a breakdown product of GFAP, visinin-like protein-1 (VILP-1), neuron specific enolase (NSE), S100 calcium-binding protein B (S100B), glutamate decarboxylase 1 (GAD1), glutamate decarboxylase 2 (GAD2), or a combination of the aforementioned proteins;

an intermediate agent for detecting one or more intermediate biomarkers present in said first biological sample from the subject and released into said first biological sample by the injury, disease, or repair and the intermediate biomarkers having an intermediate peak amount after the early peak biomarkers amount and from 48 hours to 10 days of the injury, disease, or repair; the one or more intermediate biomarkers is α-internexin (α-INT), neurofilament protein-heavy chain (NF-H), neurofilament protein-medium chain (NF-M), neurofilament protein-light chain (NF-L), synaptic damage marker synapsin isoforms (synapsin-1, synapsin-2, synapsin-3, synaptic vesicle glycoprotein 2A), myelin basic protein (MBP), myelin oligodendrocyte glycoprotein (MOG), myelin oligodendrocyte associated protein (MAG), proteolipid protein (PLP), complement proteins (C3, C4, C5, and C1q, C5b-9, CD68, CR3, C3b, iC3b), CD11b, TREM2, SIRPα, Nogo-66 receptor, DEC205, CX3CR1, CD68, CD45, CD47 or combinations of the forementioned proteins; and a late agent for detecting one or more late biomarkers present in said first biological sample from the subject and released into said first biological sample by the injury, disease, or repair and the late biomarkers having a late peak amount after the intermediate biomarkers peak amount more than 10 days of the injury, disease, or repair; the one or more late biomarkers is Tau, P-tau isoforms, TDP-43, IL-6, or combinations of the aforementioned proteins;

analyzing said first biological sample to detect amounts of the one or more early, intermediate, and late biomarkers present in said biological sample associated with of the injury, disease, or repair; and measuring Tau or P-Tau isoforms for low phosphorylation levels of at least one Tau site of Ser-181, Ser-202, Ser-205, Thr-231, Ser-396, or Ser-404.

* * * * *